(12) United States Patent
Ono et al.

(10) Patent No.: US 8,232,052 B2
(45) Date of Patent: Jul. 31, 2012

(54) METHODS OF SELECTING A DOPAMINERGIC NEURON PROLIFERATIVE PROGENITOR CELLS USING LRP4/CORIN MARKERS

(75) Inventors: Yuichi Ono, Kyoto (JP); Yasuko Nakagawa, Kyoto (JP); Yoshimasa Sakamoto, Kyoto (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 41 days.

(21) Appl. No.: 12/868,598

(22) Filed: Aug. 25, 2010

(65) Prior Publication Data
US 2010/0323366 A1 Dec. 23, 2010

Related U.S. Application Data

(62) Division of application No. 12/110,111, filed on Apr. 25, 2008, now Pat. No. 7,807,371, which is a division of application No. 10/543,003, filed as application No. PCT/JP2004/000629 on Jan. 23, 2004, now abandoned.

(30) Foreign Application Priority Data

Jan. 24, 2003 (JP) ................................. 2003-016790

(51) Int. Cl.
*C12Q 1/68* (2006.01)
(52) U.S. Cl. ........................................ 435/6.1; 435/6.11
(58) Field of Classification Search ................... None
See application file for complete search history.

(56) References Cited

U.S. PATENT DOCUMENTS

| 6,277,820 | B1 | 8/2001 | Rosenthal et al. |
| 7,622,270 | B2 | 11/2009 | Nakagawa et al. |
| 2005/0175997 | A1 | 8/2005 | Ono et al. |
| 2006/0239978 | A1 | 10/2006 | Nakagawa et al. |
| 2007/0254281 | A1 | 11/2007 | Ono et al. |
| 2008/0199437 | A1 | 8/2008 | Sakamoto et al. |
| 2010/0028866 | A1 | 2/2010 | Ono et al. |
| 2010/0203505 | A1 | 8/2010 | Ono et al. |
| 2010/0203570 | A1 | 8/2010 | Nakagawa et al. |

FOREIGN PATENT DOCUMENTS

| EP | 1 950 292 A1 | 7/2008 |
| JP | 2002-517253 | 6/2002 |
| JP | 418877 B2 | 7/2006 |
| WO | WO 99/64608 A1 | 12/1999 |
| WO | WO 00/06700 A1 | 2/2000 |
| WO | WO 01/57194 A2 | 8/2001 |
| WO | WO 02/103007 A1 | 12/2002 |
| WO | WO 2004/038018 A1 | 5/2004 |

OTHER PUBLICATIONS

Ang, S-L., "Transcriptional control of midbrain dopaminergic neuron development," *Development*, vol. 133, pp. 3499-3506 (2006).

Barberi, Tiziano et al.; "Neural subtype specification of fertilization and nuclear transfer embryonic stem cells and application in parkinsonian mice"; *Nature Biotechnology*; Oct. 2003; pp. 1200-1207; vol. 21, No. 10.

Bjorklunk, Lars M. et al.; "Embryonic stem cells develop into functional dopaminergic neurons after transplantation in a Parkinson rat model"; *PNAS*; Feb. 19, 2002; pp. 2344-2349; vol. 99, No. 4.

Hooper, J. D. et al.; "Localization of the mosaic transmembrane serine protease corin to heart myocytes"; *Eur. J. Biochem.*; 2000; pp. 6931-6937; vol. 267, No. 23.

Kawasaki, Hiroshi et al.; "Generation of dopaminergic neurons and pigmented epithelia from primate ES cells by stromal cell-derived inducing activity"; *PNAS*; Feb. 5, 2002; pp. 1580-1585; vol. 99, No. 3.

Kim, Jong-Hoon et al.; "Dopamine neurons derived from embryonic stem cells function in an animal model of Parkinson's disease"; *Nature*; Jul. 4, 2002; pp. 50-56; vol. 418.

Lee, Sang-Hun et al.; "Efficient generation of midbrain and hindbrain neurons from mouse embryonic stem cells"; *Nature Biotechnology*; Jun. 2000; pp. 675-679; vol. 18.

Sawamoto, Kazunobu et al.; "Visualization, direct isolation, and transplantation of midbrain dopaminergic neurons"; *PNAS*, May 22, 2001; pp. 6423-6428; vol. 98, No. 11.

Sawamoto, Kazunobu et al.; "Generation of dopaminergic neurons in the adult brain from mesencephalic precursor cells labeled with a *nestin-GFP* transgene"; *The Journal of Neuroscience*; Jun. 1, 2001; pp. 3895-3903; vol. 21, No. 11.

Studer, Lorenz et al.; "Transplantation of expanded mesencephalic precursors leads to recovery in parkinsonian rats"; *Nature Neuroscience*; Aug. 1998; pp. 290-295; vol. 1, No. 4.

Tomita, Y et al.; "A novel low-density lipoprotein receptor-related protein with type II membrane protein-like structure is abundant in the heart"; *J. Biochem.*; 1998; pp. 784-789; vol. 124, No. 4.

Yan, W. et al.; "Corin, a mosaic transmembrane serine protease encoded by a novel cDNA from human heart"; *J. Biol. Chem.*; 1999; pp. 14926-14935; vol. 274, No. 21.

International Search Report issued for PCT/JP04/000629 dated Mar. 9, 2004.

Office Action issued for Japanese Application No. JP2005-508128 dated Jan. 18, 2010.

Final Rejection issued for Japanese Application No. JP2005-508128 dated Mar. 31, 2010.

U.S. Appl. No. 13/352,241, filed Jan. 17, 2012, 62 pages.

*Primary Examiner* — Robert Landsman
(74) *Attorney, Agent, or Firm* — Kilpatrick Townsend & Stockton LLP

(57) ABSTRACT

In neuron transplantation therapy, in terms of safety, it is preferable to use a cell population consisting only of a desired type of cells, and to use postmitotic neurons in consideration to avoid the risk of tumorigenesis. Moreover, greater therapeutic effects would be expected through the use of earlier progenitor cells in consideration of post-transplantation viability, proper network formation ability, and such.

According to the present invention, Lrp4, a gene that is specifically expressed in dopaminergic neuron proliferative progenitor cells prior to cell cycle exit, was identified. The use of Lrp4 expression in cells as an index allows for the isolation of cells suitable for transplantation therapy of neurodegenerative diseases such as Parkinson's disease in terms of safety, survival rate, and network formation ability.

4 Claims, 8 Drawing Sheets

Lrp4

TH

Shh

NCAM

C. SPINAL CORD

D. MIDBRAIN

```
                         SEQUENCE LISTING

<160> NUMBER OF SEQ ID NOS: 20

<210> SEQ ID NO 1
<211> LENGTH: 4864
<212> TYPE: DNA
<213> ORGANISM: Mus musculus
<220> FEATURE:
<223> OTHER INFORMATION: low density lipoprotein receptor-related
      protein 4 (Lrp4), corin

<400> SEQUENCE: 1
ctagtcccca ggcagacggt ccctcactcc tgtggcttgg cgtcggagac gctggcagtc      60
atgggcaggg tttccttcag cgttcgggtc agctccgtgc ggagagcccg ctgctcttgt     120 cctggcgat gctacctctc ctgcagagtc cctccaacca ccgccctccg tgcactgaac      180
ggtcttggct gcgcggggggt tccgggggag actgcaggtg gagccgtcgg acccggcccc    240
ttggggaccc gtggcttcct ctccgggtcc aagttccagg ctcccggcag ctggaaggat    300
tgctttggag ccccgcctgc tccagacgtc ttgagagcag acaggagcgt gggcgagggc    360
tgtcctcaga agctggtgac tgctaacttg ctgcgcttcc tcctgctggt gctcatcccc    420
tgcatctgcg ccctcatcgt gctgctggcc atcctgctgt cctttgtggg aacattaaaa    480
agggtttatt tcaaatcaaa tgacagtgaa cctttggtca ctgatgggga agctcgagtg    540
cctggtgtta ttcctgtaaa tacagtttat tatgagaaca caggggcgcc ctctctgccc    600
cccagccagt ccactccagc ctggacaccg agagctcctt ctccagagga ccagagtcac    660
aggaacacaa gcacctgcat gaacatcact cacagccagt gtcaaattct gccctaccac    720
agcacgttgg cacctctctt gccaattgtc aaaaacatgg acatggagaa gttcctcaag    780
ttcttcacgt acctccatcg cctcagttgc tatcaacata tcctgctctt cggctgtagc    840
ctcgccttcc ctgagtgcgt tgttgatggc gatgacaggc atggtcttct accctgtaga    900
```

```
tctttctgtg aggctgcaaa agaaggatgc gaatctgtcc tgggaatggt gaactcctcc    960
tggccggatt ccctcagatg ctctcagttt agggaccaca ctgagactaa cagcagtgtc   1020
agaaagagct gcttctcact gcagcaggaa catggaaagc aatcactctg tggaggggc    1080 gagagcttcc tgtgtaccag cgggctctgc gtcccaaga agctgcagtg taacggctat   1140
aatgactgtg atgactggag cgacgaggcg cattgcaact gcagcaagga tctgtttcac   1200
tgtggcacag gcaagtgcct ccactacagc ctcttgtgtg atgggtacga tgactgtggg   1260
gacccgagtg acgagcaaaa ctgtgattgt aatctcacaa aagagcatcg ctgtggagat   1320
gggcgctgca ttgcggctga gtgggtgtgc gatgggacc atgactgtgt ggacaagtct   1380
gatgaggtca actgctcttg tcacagccag ggcctggtgg aatgcacaag tggacagtgc   1440
atccctagca ccttccagtg tgatgggac gaagactgta aggatgggag tgacgaggag   1500
aactgcagtg acagtcagac gccatgtcca aaggagaaac agggatgctt tggcagttcc   1560
tgcgtcgaat cctgtgctgg tagctctctg tgtgactcag acagcagcct gagtaactgc   1620
agtcaatgtg agcccatcac tttggaactc tgcatgaatt tgctctacaa ccatacacat   1680
tatccaaatt accttggcca cagaactcaa aaggaagcgt ccatcagctg ggagtcatcc   1740
cttttccctg cccttgtaca aaccaactgt tacaaatacc tcatgttttt cgcttgcacc   1800
attttggttc caaagtgtga tgtgaataca ggacaacgca tcccgccttg cagactcctg   1860
tgtgagcact ccaaagagcg ctgtgagtct gttctgggaa tcgttggcct gcagtggcct   1920
gaagacaccg actgcaatca atttccagag gaaagttcag acaatcaaac ttgcctcctg   1980
cccaatgaag atgtggaaga tgctctccg agtcacttca aatgccgctc gggacgatgc   2040
gttctgggct ccaggagatg tgacggccag gctgactgtg acgacgacag tgacgaggag   2100
aactgtggtt gtaaagagag agctctttgg gaatgtccat taataagca atgtctgaag   2160 catacattaa tctgcgatgg gttccagat tgtccagaca gtatggatga aaaaaactgc   2220
tcattttgcc aagacaatga gctggaatgt gccaaccatg agtgtgtgcc gcgtgacctt   2280
tggtgcgacg gatgggtcga ctgctcagac agttctgatg aatggggctg tgtgaccctc   2340
tctaaaaatg ggaactcctc ctcattgctg actgttcaca aatctgcaaa ggaacaccac   2400
gtgtgtgctg acggctggcg ggagacgttg agtcagctgg cctgcaagca gatgggttta   2460
ggagaaccgt ctgtgaccaa gctgatccca ggacaggaag gccagcagtg gctgaggttg   2520 tacccccaact gggagaatct caatgggagc accttgcagg agctgctggt atacaggcac   2580
tcctgcccaa gcagaagtga gatttccctt ctgtgctcca gcaagactg tggccgccgc   2640 cctgctgccc gaatgaacaa gaggatcctt gggggtcgga ctagtcgtcc tgggaggtgg   2700
ccgtggcagt gctctctgca gagtgaaccc agtggacata tctgtggctg tgtcctcatt   2760
gccaagaagt gggtcctgac agttgcccat tgctttgaag ggagagaaga cgctgatgtt   2820
tggaaagtgg tatttggcat aaacaacctg gaccatccat caggcttcat gcagacccgc   2880
tttgtgaaga ccatcctgct acatccccgt tacagtcgag cagtggtaga ctatgatatc   2940
agcgtggtgg agctgagcga tgatatcaat gagacaagct acgtcagacc tgtctgccta   3000
cccagtccgg aggagtatct agaaccagat acgtactgct acatcacagg ctggggccac   3060
atgggcaata aaatgccctt taagctgcag gagggagagg tccgcattat ccctctggag   3120
cagtgccagt cctattttga catgaagacc atcaccaatc ggatgatctg tgctggctat   3180
gagtctggca ccgtggactc ctgcatggga gacagcggtg ggcctctggt ttgtgaacga   3240
cccggaggac agtggacatt atttggttta acttcatggg gctccgtctg cttttccaaa   3300
```

-continued

| | |
|---|---|
| gttctgggac ctggagtgta cagcaatgtg tcttactttg tgggctggat tgaaagacaa | 3360 |
| atatatatcc agacctttct ccaaaagaaa tcccaaggat aatcagagac tttgtgggga | 3420 |
| aacctacatg gagaatgacc ctctgaaaca gaagcttgtc ctgccaagag ctgtacgaac | 3480 |
| aggcgtttca cggacaggac gctcaacatg caccgcaaga tctctcctgt ttgtgctaga | 3540 |
| tgagttttac tcaggcttta atctctttca acattatcat ttattaattt catgaatcct | 3600 |
| tttaaaagca cagagcaaag taggttttgt tattttgcta ggctaacctt gaatgtagtg | 3660 |
| tgcaattacc aacccataga gacatttgga gctctagggt aacaagttat agaaagctcc | 3720 |
| ttttattact actacaagac acacacggag atacacgctg actgatctcc agtttctgct | 3780 |
| taagcccagt ggcttagggg gcacatttca gaactgatct tggagactgg cttttaattt | 3840 |
| gtagaaagcc aagagaatat atatgctttt attatttact ctactcttct aaataacttg | 3900 |
| aagaaatcat gaaagacaga gaaaggaccc acagtgttga tctagacagt tgaagttgca | 3960 |
| agaatgtaaa attctctagc caaccaaact aacactctga agtaagtaga attctatcct | 4020 |
| ttctgtattc aaattaagct taaaatctcc accagatttg ttcccgttac tgggaatttt | 4080 |
| cggagtatgt cacttagatg actgtgatgt caaaagccag gtcaatcctt gaggaaataa | 4140 |
| tttgtttgct tatgtgggaa tgaataagaa tctttccatt ccgcaaaaca cacaaattaa | 4200 |
| aaaggagaaa aaaattaaa taacattcca cacccaatta attctgaaaa ttagtctgct | 4260 |
| tgtattcacc caaaacagaa aagttacaga aatatatttc aaagtgcagc aaaatgttgc | 4320 |
| atggagtata taacattttg caatttcccc ctcatgatgt ctaacatccg gtattgccat | 4380 |
| ttgcctcatt gataattaaa actaaatttt aaggatgctt ttaagcactg ggccacttta | 4440 |
| tgggaatcaa ttcccaaagc aattagtggt tacaagtatt ttttcccact aaaaagtttc | 4500 |
| aaaacacaaa ccttcatact aaattaatta gccagacatg aactatgtaa catgcaaatg | 4560 |
| cctttttgaa caagtaggat gcactgttaa acttcaccag caaccaaact gcctcagtat | 4620 |
| tgcttacagg gactacctgc aatttatat gtgtattttg tactcttttt ctagatagtt | 4680 |
| caaatgcaaa acattgtttc aacccctatt ctccatgttg ttcacctctt gtcctggaat | 4740 |
| ttgttacaaa gtgtgtgtag caaatgattg tactgcggtc aggactatat gaaggtttag | 4800 |
| gaccatcggg tcggttttgt tataattgtt ggcacataat taataaaata tttttagcat | 4860 |
| tggg | 4864 |

<210> SEQ ID NO 2
<211> LENGTH: 4933
<212> TYPE: DNA
<213> ORGANISM: Homo sapiens
<220> FEATURE:
<223> OTHER INFORMATION: low density lipoprotein receptor-related
    protein 4 (LRP4), multiple epidermal growth factor-like domains 7
    (MEGF7), LRP10

<400> SEQUENCE: 2

| | |
|---|---|
| aaatcatccg tagtgcctcc ccgggggaca cgtagaggag agaaaagcga ccaagataaa | 60 |
| agtggacaga agaataagcg agacttttta tccatgaaac agtctcctgc cctcgctccg | 120 |
| gaagagcgct accgcagagc cgggtcccca agccggtct tgagagctga tgacaataac | 180 |
| atgggcaatg gctgctctca gaagctggcg actgctaacc tctccggtt cctattgctg | 240 |
| gtcctgattc catgtatctg tgctctcgtt ctcttgctgg tgatcctgct ttcctatgtt | 300 |
| ggaacattac aaaaggtcta ttttaaatca aatgggagtg aacctttggt cactgatggt | 360 |
| gaaatccaag ggtccgatgt tattcttaca aatacaattt ataaccagag cactgtggtg | 420 |

```
tctactgcac atcccgacca acacgttcca gcctggacta cggatgcttc tctcccaggg    480
gaccaaagtc acaggaatac aagtgcctgt atgaacatca cccacagcca gtgtcagatg    540
ctgccctacc acgccacgct gacacctctc ctctcagttg tcagaaacat ggaaatggaa    600
aagttcctca gttttttcac atatctccat cgcctcagtt gctatcaaca tatcatgctg    660
tttggctgta ccctcgcctt ccctgagtgc atcattgatg gcgatgacag tcatggactc    720
ctgccctgta ggtccttctg tgaggctgca aagaaggct gtgaatcagt cctggggatg     780
gtgaattact cctggccgga tttcctcaga tgctcccagt ttagaaacca aactgaaagc    840
agcaatgtca gcagaatttg cttctcacct cagcaggaaa acggaaagca attgctctgt    900
ggaaggggtg agaactttct gtgtgccagt ggaatctgca tccccgggaa actgcaatgt    960
aatggctaca cgactgtga cgactggagt gacgaggctc attgcaactg cagcgagaat    1020
ctgtttcact gtcacacagg caagtgcctt aattacagcc ttgtgtgtga tggatatgat    1080
gactgtgggg atttgagtga tgagcaaaac tgtgattgca atcccacaac agagcatcgc    1140
tgcggggacg ggcgctgcat cgccatggag tgggtgtgtg atggtgacca cgactgtgtg    1200
gataagtccg acgaggtcaa ctgctcctgt cacagccagg gtctggtgga atgcagaaat    1260
ggacaatgta tccccagcac gtttcaatgt gatggtgacg aggactgcaa ggatgggagt    1320
gatgaggaga actgcagcgt cattcagact tcatgtcaag aaggagacca agatgcctc    1380 tacaatccct gccttgattc atgtggtggt agctctctct gtgacccgaa caacagtctg    1440
aataactgta gtcaatgtga accaattaca ttggaactct gcatgaattt gccctacaac    1500
agtacaagtt atccaaatta ttttggccac aggactcaaa aggaagcatc catcagctgg    1560
gagtcttctc ttttccctgc acttgttcaa accaactgtt ataaatacct catgttcttt    1620
tcttgcacca ttttggtacc aaaatgtgat gtgaatacag gcgagcgtat ccctccttgc    1680
agggcattgt gtgaacactc taaagaacgc tgtgagtctg ttcttgggat tgtgggccta    1740
cagtggcctg aagacacaga ttgcagtcaa tttccagagg aaaattcaga caatcaaacc    1800
tgcctgatgc ctgatgaata tgtggaagaa tgctcaccta gtcatttcaa gtgccgctca    1860
ggacagtgtg ttctggcttc cagaagatgt gatggccagg ccgactgtga cgatgacagt    1920
gatgaggaaa actgtggttg taaagagaga gatctttggg aatgtccatc caataaacaa    1980
tgtttgaagc acacagtgat ctgcgatggg ttcccagact gccctgatta catggacgag    2040
aaaaactgct cattttgcca agatgatgag ctggaatgtg caaaccatgc gtgtgtgtca    2100
cgtgacctgt ggtgtgatgg tgaagccgac tgctcagaca gttcagatga atgggactgt    2160
gtgaccctct ctataaatgt gaactcctct tcctttctga tggttcacag agctgccaca    2220
gaacaccatg tgtgtgcaga tggctggcag gagatattga gtcagctggc ctgcaagcag    2280
atgggtttag gagaaccatc tgtgaccaaa ttgatacagg aacaggagaa agagccgcgg    2340
tggctgacat tacactccaa ctgggagagc ctcaatggga ccactttaca tgaacttcta    2400
gtaaatgggc agtcttgtga gagcagaagt aaaatttctc ttctgtgtac taaacaagac    2460
tgtgggcgcc gccctgctgc ccgaatgaac aaaaggatcc ttggaggtcg acgagtcgc    2520 cctggaaggt ggccatggca gtgttctctg cagagtgaac ccagtggaca tatctgtggc    2580
tgtgtcctca ttgccaagaa gtgggttctg acagttgccc actgcttcga ggggagagag    2640
aatgctgcag tttggaaagt ggtgcttggc atcaacaatc tagaccatcc atcagtgttc    2700
atgcagacac gctttgtgaa gaccatcatc ctgcatcccc gctacagtcg agcagtggtg    2760
gactatgaca tcagcatcgt tgagctgagt gaagacatca gtgagactgg ctacgtccgg    2820
```

```
cctgtctgct tgcccaaccc ggagcagtgg ctagagcctg acacgtactg ctatatcaca    2880
ggctggggcc acatgggcaa taaaatgcca tttaagctgc aagagggaga ggtccgcatt    2940
atttctctgg aacattgtca gtcctacttt gacatgaaga ccatcaccac tcggatgata    3000
tgtgctggct atgagtctgg cacagttgat tcatgcatgg gtgacagcgg tgggcctctt    3060
gtttgtgaga agcctggagg acggtggaca ttatttggat taacttcatg gggctccgtc    3120
tgcttttcca aagtcctggg gcctggcgtt tatagtaatg tgtcatattt cgtcgaatgg    3180
attaaaagac agatttacat ccagaccttt ctcctaaact aattataagg atgatcagag    3240
acttttgcca gctacactaa aagaaaatgg ccttcttgac tgtgaagagc tgcctgcaga    3300
gagctgtaca gaagcacttt tcatggacag aaatgctcaa tcgtgcactg caaatttgca    3360
tgtttgtttt ggactaattt ttttcaattt attttttcac cttcattttt ctcttatttc    3420
aagttcaatg aaagacttta caaaagcaaa caaagcagac tttgtccttt tgccaggcct    3480
aaccatgact gcagcacaaa attatcgact ctggcgagat ttaaaatcag gtgctacagt    3540
aacaggttat ggaatggtct cttttatcct atcacaaaaa aagacataga tatttaggct    3600
gattaattat ctctaccagt ttttgtttct caagctcagt gcatagtggt aaatttcagt    3660
gttaacattg gagacttgct tttctttttc ttttttttata ccccacaatt cttttttatt    3720
acacttcgaa ttttagggta cacgagcaca acgtgcaggt tagttacata tgtatacatg    3780
tgccatgttg gtgtgctgaa cccagtaact cgtcatttga tttattaaaa gccaagataa    3840
tttacatgtt taaagtattt actattaccc ccttctaatg tttgcataat tctgagaact    3900
gataaaagac agcaataaaa gaccagtgtc atccatttag gtagcaagac atattgaatg    3960
caaagttctt tagatatcaa tattaacact tgacattatt ggacccccca ttctggatgt    4020
atatcaagat cataatttta tagaagagtc tctatagaac tgtcctcata gctgggtttg    4080
ttcaggatat atgagttggc tgattgagac tgcaacaact acatctatat ttatgggcaa    4140
tattttgttt tacttatgtg gcaaagaact ggatattaaa ctttgcaaaa gagaatttag    4200
atgagagatg caatttttta aaagaaaat taatttgcat ccctcgttta attaaattta    4260
ttttcagtt ttcttgcgtt catccatacc aacaaagtca taaagagcat attttagagc    4320
acagtaagac tttgcatgga gtaaaacatt ttgtaatttt cctcaaaaga tgtttaatat    4380
ctggtttctt ctcattggta attaaaattt tagaaatgat ttttagctct aggccacttt    4440
acgcaactca atttctgaag caattagtgg taaaaagtat ttttccccac taaaaaactt    4500
taaaacacaa atcttcatat atacttaatt taattagtca ggcatccatt ttgccttta    4560
aacaactagg attccctact aacctccacc agcaacctgg actgcctcag cattccaaat    4620
agatactacc tgcaatttta tacatgtatt tttgtatctt ttctgtgtgt aaacatagtt    4680
gaaattcaaa aagttgtagc aatttctata ctattcatct cctgtccttc agtttgtata    4740
aacctaagga gagtgtgaaa tccagcaact gaattgtggt cacgattgta tgaaagttca    4800
agaacatatg tcagttttgt tacagttgta gctacatact caatgtatca acttttagcc    4860
tgctcaactt aggctcagtg aaatatatat attatactta ttttaaataa ttcttaatac    4920
aaataaaatg gta                                                      4933
```

<210> SEQ ID NO 3
<211> LENGTH: 1113
<212> TYPE: PRT
<213> ORGANISM: Mus musculus
<220> FEATURE:
<223> OTHER INFORMATION: low density lipoprotein receptor-related
      protein 4 (Lrp4), corin

```
<400> SEQUENCE: 3

Met Gly Arg Val Ser Phe Ser Val Arg Val Ser Val Arg Arg Ala
1               5                   10                  15

Arg Cys Ser Cys Pro Gly Arg Cys Tyr Leu Ser Cys Arg Val Pro Pro
                20                  25                  30

Thr Thr Ala Leu Arg Ala Leu Asn Gly Leu Gly Cys Ala Gly Val Pro
            35                  40                  45

Gly Glu Thr Ala Gly Gly Ala Val Gly Pro Gly Pro Leu Gly Thr Arg
        50                  55                  60

Gly Phe Leu Ser Gly Ser Lys Phe Gln Ala Pro Gly Ser Trp Lys Asp
65                  70                  75                  80

Cys Phe Gly Ala Pro Pro Ala Pro Asp Val Leu Arg Ala Asp Arg Ser
                85                  90                  95

Val Gly Glu Gly Cys Pro Gln Lys Leu Val Thr Ala Asn Leu Leu Arg
            100                 105                 110

Phe Leu Leu Leu Val Leu Ile Pro Cys Ile Cys Ala Leu Ile Val Leu
        115                 120                 125

Leu Ala Ile Leu Leu Ser Phe Val Gly Thr Leu Lys Arg Val Tyr Phe
130                 135                 140

Lys Ser Asn Asp Ser Glu Pro Leu Val Thr Asp Gly Glu Ala Arg Val
145                 150                 155                 160

Pro Gly Val Ile Pro Val Asn Thr Val Tyr Tyr Glu Asn Thr Gly Ala
                165                 170                 175

Pro Ser Leu Pro Pro Ser Gln Ser Thr Pro Ala Trp Thr Pro Arg Ala
            180                 185                 190

Pro Ser Pro Glu Asp Gln Ser His Arg Asn Thr Ser Thr Cys Met Asn
        195                 200                 205

Ile Thr His Ser Gln Cys Gln Ile Leu Pro Tyr His Ser Thr Leu Ala
210                 215                 220

Pro Leu Leu Pro Ile Val Lys Asn Met Asp Met Glu Lys Phe Leu Lys
225                 230                 235                 240

Phe Phe Thr Tyr Leu His Arg Leu Ser Cys Tyr Gln His Ile Leu Leu
                245                 250                 255

Phe Gly Cys Ser Leu Ala Phe Pro Glu Cys Val Val Asp Gly Asp Asp
            260                 265                 270

Arg His Gly Leu Leu Pro Cys Arg Ser Phe Cys Glu Ala Ala Lys Glu
        275                 280                 285

Gly Cys Glu Ser Val Leu Gly Met Val Asn Ser Ser Trp Pro Asp Ser
290                 295                 300

Leu Arg Cys Ser Gln Phe Arg Asp His Thr Glu Thr Asn Ser Ser Val
305                 310                 315                 320

Arg Lys Ser Cys Phe Ser Leu Gln Gln Glu His Gly Lys Gln Ser Leu
                325                 330                 335

Cys Gly Gly Gly Glu Ser Phe Leu Cys Thr Ser Gly Leu Cys Val Pro
            340                 345                 350

Lys Lys Leu Gln Cys Asn Gly Tyr Asn Asp Cys Asp Asp Trp Ser Asp
        355                 360                 365

Glu Ala His Cys Asn Cys Ser Lys Asp Leu Phe His Cys Gly Thr Gly
370                 375                 380

Lys Cys Leu His Tyr Ser Leu Leu Cys Asp Gly Tyr Asp Asp Cys Gly
385                 390                 395                 400

Asp Pro Ser Asp Glu Gln Asn Cys Asp Cys Asn Leu Thr Lys Glu His
                405                 410                 415
```

```
Arg Cys Gly Asp Gly Arg Cys Ile Ala Ala Glu Trp Val Cys Asp Gly
            420                 425                 430

Asp His Asp Cys Val Asp Lys Ser Asp Glu Val Asn Cys Ser Cys His
            435                 440                 445

Ser Gln Gly Leu Val Glu Cys Thr Ser Gly Gln Cys Ile Pro Ser Thr
            450                 455                 460

Phe Gln Cys Asp Gly Asp Glu Asp Cys Lys Asp Gly Ser Asp Glu Glu
465                 470                 475                 480

Asn Cys Ser Asp Ser Gln Thr Pro Cys Pro Glu Gly Glu Gln Gly Cys
            485                 490                 495

Phe Gly Ser Ser Cys Val Glu Ser Cys Ala Gly Ser Ser Leu Cys Asp
            500                 505                 510

Ser Asp Ser Ser Leu Ser Asn Cys Ser Gln Cys Glu Pro Ile Thr Leu
            515                 520                 525

Glu Leu Cys Met Asn Leu Leu Tyr Asn His Thr His Tyr Pro Asn Tyr
            530                 535                 540

Leu Gly His Arg Thr Gln Lys Glu Ala Ser Ile Ser Trp Glu Ser Ser
545                 550                 555                 560

Leu Phe Pro Ala Leu Val Gln Thr Asn Cys Tyr Lys Tyr Leu Met Phe
            565                 570                 575

Phe Ala Cys Thr Ile Leu Val Pro Lys Cys Asp Val Asn Thr Gly Gln
            580                 585                 590

Arg Ile Pro Pro Cys Arg Leu Leu Cys Glu His Ser Lys Glu Arg Cys
            595                 600                 605

Glu Ser Val Leu Gly Ile Val Gly Leu Gln Trp Pro Glu Asp Thr Asp
            610                 615                 620

Cys Asn Gln Phe Pro Glu Glu Ser Ser Asp Asn Gln Thr Cys Leu Leu
625                 630                 635                 640

Pro Asn Glu Asp Val Glu Glu Cys Ser Pro Ser His Phe Lys Cys Arg
            645                 650                 655

Ser Gly Arg Cys Val Leu Gly Ser Arg Arg Cys Asp Gly Gln Ala Asp
            660                 665                 670

Cys Asp Asp Asp Ser Asp Glu Glu Asn Cys Gly Cys Lys Glu Arg Ala
            675                 680                 685

Leu Trp Glu Cys Pro Phe Asn Lys Gln Cys Leu Lys His Thr Leu Ile
            690                 695                 700

Cys Asp Gly Phe Pro Asp Cys Pro Asp Ser Met Asp Glu Lys Asn Cys
705                 710                 715                 720

Ser Phe Cys Gln Asp Asn Glu Leu Glu Cys Ala Asn His Glu Cys Val
            725                 730                 735

Pro Arg Asp Leu Trp Cys Asp Gly Trp Val Asp Cys Ser Asp Ser Ser
            740                 745                 750

Asp Glu Trp Gly Cys Val Thr Leu Ser Lys Asn Gly Asn Ser Ser Ser
            755                 760                 765

Leu Leu Thr Val His Lys Ser Ala Lys Glu His Val Cys Ala Asp
            770                 775                 780

Gly Trp Arg Glu Thr Leu Ser Gln Leu Ala Cys Lys Gln Met Gly Leu
785                 790                 795                 800

Gly Glu Pro Ser Val Thr Lys Leu Ile Pro Gly Gln Glu Gly Gln Gln
            805                 810                 815

Trp Leu Arg Leu Tyr Pro Asn Trp Glu Asn Leu Asn Gly Ser Thr Leu
            820                 825                 830

Gln Glu Leu Leu Val Tyr Arg His Ser Cys Pro Ser Arg Ser Glu Ile
```

-continued

```
                835                 840                 845
Ser Leu Leu Cys Ser Lys Gln Asp Cys Gly Arg Arg Pro Ala Ala Arg
    850                 855                 860

Met Asn Lys Arg Ile Leu Gly Gly Arg Thr Ser Arg Pro Gly Arg Trp
865                 870                 875                 880

Pro Trp Gln Cys Ser Leu Gln Ser Glu Pro Ser Gly His Ile Cys Gly
                885                 890                 895

Cys Val Leu Ile Ala Lys Lys Trp Val Leu Thr Val Ala His Cys Phe
            900                 905                 910

Glu Gly Arg Glu Asp Ala Asp Val Trp Lys Val Val Phe Gly Ile Asn
        915                 920                 925

Asn Leu Asp His Pro Ser Gly Phe Met Gln Thr Arg Phe Val Lys Thr
    930                 935                 940

Ile Leu Leu His Pro Arg Tyr Ser Arg Ala Val Val Asp Tyr Asp Ile
945                 950                 955                 960

Ser Val Val Glu Leu Ser Asp Asp Ile Asn Glu Thr Ser Tyr Val Arg
                965                 970                 975

Pro Val Cys Leu Pro Ser Pro Glu Glu Tyr Leu Glu Pro Asp Thr Tyr
            980                 985                 990

Cys Tyr Ile Thr Gly Trp Gly His  Met Gly Asn Lys Met Pro Phe Lys
        995                 1000                1005

Leu Gln  Glu Gly Glu Val Arg  Ile Ile Pro Leu Glu  Gln Cys Gln
    1010                1015                1020

Ser Tyr  Phe Asp Met Lys Thr  Ile Thr Asn Arg Met  Ile Cys Ala
    1025                1030                1035

Gly Tyr  Glu Ser Gly Thr Val  Asp Ser Cys Met Gly  Asp Ser Gly
    1040                1045                1050

Gly Pro  Leu Val Cys Glu Arg  Pro Gly Gly Gln Trp  Thr Leu Phe
    1055                1060                1065

Gly Leu  Thr Ser Trp Gly Ser  Val Cys Phe Ser Lys  Val Leu Gly
    1070                1075                1080

Pro Gly  Val Tyr Ser Asn Val  Ser Tyr Phe Val Gly  Trp Ile Glu
    1085                1090                1095

Arg Gln  Ile Tyr Ile Gln Thr  Phe Leu Gln Lys Lys  Ser Gln Gly
    1100                1105                1110
```

<210> SEQ ID NO 4
<211> LENGTH: 1042
<212> TYPE: PRT
<213> ORGANISM: Homo sapiens
<220> FEATURE:
<223> OTHER INFORMATION: low density lipoprotein receptor-related
      protein 4 (LRP4), multiple epidermal growth factor-like domains 7
      (MEGF7), LRP10

<400> SEQUENCE: 4

```
Met Lys Gln Ser Pro Ala Leu Ala Pro Glu Glu Arg Tyr Arg Arg Ala
1               5                   10                  15

Gly Ser Pro Lys Pro Val Leu Arg Ala Asp Asp Asn Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Val Ile
    50                  55                  60

Leu Leu Ser Tyr Val Gly Thr Leu Gln Lys Val Tyr Phe Lys Ser Asn
65                  70                  75                  80
```

```
Gly Ser Glu Pro Leu Val Thr Asp Gly Glu Ile Gln Gly Ser Asp Val
                85                  90                  95

Ile Leu Thr Asn Thr Ile Tyr Asn Gln Ser Thr Val Val Ser Thr Ala
                100                 105                 110

His Pro Asp Gln His Val Pro Ala Trp Thr Thr Asp Ala Ser Leu Pro
                115                 120                 125

Gly Asp Gln Ser His Arg Asn Thr Ser Ala Cys Met Asn Ile Thr His
        130                 135                 140

Ser Gln Cys Gln Met Leu Pro Tyr His Ala Thr Leu Thr Pro Leu Leu
145                 150                 155                 160

Ser Val Val Arg Asn Met Glu Met Glu Lys Phe Leu Lys Phe Phe Thr
                165                 170                 175

Tyr Leu His Arg Leu Ser Cys Tyr Gln His Ile Met Leu Phe Gly Cys
                180                 185                 190

Thr Leu Ala Phe Pro Glu Cys Ile Ile Asp Gly Asp Ser His Gly
                195                 200                 205

Leu Leu Pro Cys Arg Ser Phe Cys Glu Ala Ala Lys Glu Gly Cys Glu
        210                 215                 220

Ser Val Leu Gly Met Val Asn Tyr Ser Trp Pro Asp Phe Leu Arg Cys
225                 230                 235                 240

Ser Gln Phe Arg Asn Gln Thr Glu Ser Ser Asn Val Ser Arg Ile Cys
                245                 250                 255

Phe Ser Pro Gln Gln Glu Asn Gly Lys Gln Leu Leu Cys Gly Arg Gly
                260                 265                 270

Glu Asn Phe Leu Cys Ala Ser Gly Ile Cys Ile Pro Gly Lys Leu Gln
        275                 280                 285

Cys Asn Gly Tyr Asn Asp Cys Asp Asp Trp Ser Asp Glu Ala His Cys
        290                 295                 300

Asn Cys Ser Glu Asn Leu Phe His Cys His Thr Gly Lys Cys Leu Asn
305                 310                 315                 320

Tyr Ser Leu Val Cys Asp Gly Tyr Asp Asp Cys Gly Asp Leu Ser Asp
                325                 330                 335

Glu Gln Asn Cys Asp Cys Asn Pro Thr Thr Glu His Arg Cys Gly Asp
            340                 345                 350

Gly Arg Cys Ile Ala Met Glu Trp Val Cys Asp Gly Asp His Asp Cys
        355                 360                 365

Val Asp Lys Ser Asp Glu Val Asn Cys Ser Cys His Ser Gln Gly Leu
        370                 375                 380

Val Glu Cys Arg Asn Gly Gln Cys Ile Pro Ser Thr Phe Gln Cys Asp
385                 390                 395                 400

Gly Asp Glu Asp Cys Lys Asp Gly Ser Asp Glu Glu Asn Cys Ser Val
                405                 410                 415

Ile Gln Thr Ser Cys Gln Glu Gly Asp Gln Arg Cys Leu Tyr Asn Pro
                420                 425                 430

Cys Leu Asp Ser Cys Gly Gly Ser Ser Leu Cys Asp Pro Asn Asn Ser
        435                 440                 445

Leu Asn Asn Cys Ser Gln Cys Glu Pro Ile Thr Leu Glu Leu Cys Met
    450                 455                 460

Asn Leu Pro Tyr Asn Ser Thr Ser Tyr Pro Asn Tyr Phe Gly His Arg
465                 470                 475                 480

Thr Gln Lys Glu Ala Ser Ile Ser Trp Glu Ser Ser Leu Phe Pro Ala
                485                 490                 495

Leu Val Gln Thr Asn Cys Tyr Lys Tyr Leu Met Phe Phe Ser Cys Thr
                500                 505                 510
```

```
Ile Leu Val Pro Lys Cys Asp Val Asn Thr Gly Glu Arg Ile Pro Pro
            515                 520                 525
Cys Arg Ala Leu Cys Glu His Ser Lys Glu Arg Cys Glu Ser Val Leu
        530                 535                 540
Gly Ile Val Gly Leu Gln Trp Pro Glu Asp Thr Asp Cys Ser Gln Phe
545                 550                 555                 560
Pro Glu Glu Asn Ser Asp Asn Gln Thr Cys Leu Met Pro Asp Glu Tyr
                565                 570                 575
Val Glu Glu Cys Ser Pro Ser His Phe Lys Cys Arg Ser Gly Gln Cys
            580                 585                 590
Val Leu Ala Ser Arg Arg Cys Asp Gly Gln Ala Asp Cys Asp Asp Asp
        595                 600                 605
Ser Asp Glu Glu Asn Cys Gly Cys Lys Glu Arg Asp Leu Trp Glu Cys
        610                 615                 620
Pro Ser Asn Lys Gln Cys Leu Lys His Thr Val Ile Cys Asp Gly Phe
625                 630                 635                 640
Pro Asp Cys Pro Asp Tyr Met Asp Glu Lys Asn Cys Ser Phe Cys Gln
                645                 650                 655
Asp Asp Glu Leu Glu Cys Ala Asn His Ala Cys Val Ser Arg Asp Leu
            660                 665                 670
Trp Cys Asp Gly Glu Ala Asp Cys Ser Asp Ser Ser Asp Glu Trp Asp
        675                 680                 685
Cys Val Thr Leu Ser Ile Asn Val Asn Ser Ser Phe Leu Met Val
        690                 695                 700
His Arg Ala Ala Thr Glu His His Val Cys Ala Asp Gly Trp Gln Glu
705                 710                 715                 720
Ile Leu Ser Gln Leu Ala Cys Lys Gln Met Gly Leu Gly Glu Pro Ser
                725                 730                 735
Val Thr Lys Leu Ile Gln Glu Gln Lys Glu Pro Arg Trp Leu Thr
            740                 745                 750
Leu His Ser Asn Trp Glu Ser Leu Asn Gly Thr Thr Leu His Glu Leu
        755                 760                 765
Leu Val Asn Gly Gln Ser Cys Glu Ser Arg Ser Lys Ile Ser Leu Leu
        770                 775                 780
Cys Thr Lys Gln Asp Cys Gly Arg Arg Pro Ala Ala Arg Met Asn Lys
785                 790                 795                 800
Arg Ile Leu Gly Gly Arg Thr Ser Arg Pro Gly Arg Trp Pro Trp Gln
                805                 810                 815
Cys Ser Leu Gln Ser Glu Pro Ser Gly His Ile Cys Gly Cys Val Leu
            820                 825                 830
Ile Ala Lys Lys Trp Val Leu Thr Val Ala His Cys Phe Glu Gly Arg
        835                 840                 845
Glu Asn Ala Ala Val Trp Lys Val Val Leu Gly Ile Asn Asn Leu Asp
        850                 855                 860
His Pro Ser Val Phe Met Gln Thr Arg Phe Val Lys Thr Ile Ile Leu
865                 870                 875                 880
His Pro Arg Tyr Ser Arg Ala Val Val Asp Tyr Asp Ile Ser Ile Val
                885                 890                 895
Glu Leu Ser Glu Asp Ile Ser Glu Thr Gly Tyr Val Arg Pro Val Cys
            900                 905                 910
Leu Pro Asn Pro Glu Gln Trp Leu Glu Pro Asp Thr Tyr Cys Tyr Ile
        915                 920                 925
Thr Gly Trp Gly His Met Gly Asn Lys Met Pro Phe Lys Leu Gln Glu
```

-continued

```
                930             935             940
Gly Glu Val Arg Ile Ile Ser Leu Glu His Cys Gln Ser Tyr Phe Asp
945             950             955             960

Met Lys Thr Ile Thr Thr Arg Met Ile Cys Ala Gly Tyr Glu Ser Gly
                965             970             975

Thr Val Asp Ser Cys Met Gly Asp Ser Gly Gly Pro Leu Val Cys Glu
            980             985             990

Lys Pro Gly Gly Arg Trp Thr Leu  Phe Gly Leu Thr Ser  Trp Gly Ser
        995             1000            1005

Val Cys  Phe Ser Lys Val Leu  Gly Pro Gly Val Tyr  Ser Asn Val Ser
    1010            1015            1020

Tyr Phe Val Glu Trp Ile  Lys Arg Gln Ile Tyr Ile Gln Thr Phe Leu
1025            1030            1035            1040

Leu Asn

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:synthetic
      ad2S adapter for cDNA amplification

<400> SEQUENCE: 5
cagctccaca acctacatca ttccgt                                          26

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence:synthetic
      ad2A adapter for cDNA amplification

<400> SEQUENCE: 6
acggaatgat gt                                                         12

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:synthetic
      ad3S adapter for cDNA amplification

<400> SEQUENCE: 7
gtccatcttc tctctgagac tctggt                                          26

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence:synthetic
      ad3A adapter for cDNA amplification

<400> SEQUENCE: 8
accagagtct ca                                                         12

<210> SEQ ID NO 9
<211> LENGTH: 26
<212> TYPE: DNA
<213> ORGANISM: Artificial Sequence
<220> FEATURE:
```

<223> OTHER INFORMATION: Description of Artificial Sequence:synthetic
      ad4S adapter for cDNA amplification

<400> SEQUENCE: 9
ctgatgggtg tcttctgtga gtgtgt                                          26

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence:synthetic
      ad4A adapter for cDNA amplification

<400> SEQUENCE: 10
acacactcac ag                                                         12

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:synthetic
      ad5S adapter for cDNA amplification

<400> SEQUENCE: 11
ccagcatcga gaatcagtgt gacagt                                          26

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence:synthetic
      ad5A adapter for cDNA amplification

<400> SEQUENCE: 12
actgtcacac tg                                                         12

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:synthetic
      ad13S adapter for cDNA amplification

<400> SEQUENCE: 13
gtcgatgaac ttcgactgtc gatcgt                                          26

<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence:synthetic
      ad13A adapter for cDNA amplification

<400> SEQUENCE: 14
acgatcgaca gt                                                         12

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:synthetic
      Lrp4 RT-PCR primer -continued

```
<400> SEQUENCE: 15
tagtctacca ctgctcgact gtaacg                                            26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:synthetic
      Lrp4 RT-PCR primer

<400> SEQUENCE: 16
cagagtgaac ccagtggaca tatctg                                            26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence:synthetic TH
      RT-PCR primer

<400> SEQUENCE: 17
gttcccaagg aaagtgtcag agttgg                                            26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:synthetic TH
      RT-PCR primer

<400> SEQUENCE: 18
gaagctggaa agcctccagg tgttcc                                            26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:synthetic
      DAT RT-PCR primer

<400> SEQUENCE: 19
ctccgagcag acaccatgac cttagc                                            26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence:synthetic
      DAT RT-PCR primer

<400> SEQUENCE: 20
aggagtaggg cttgtctccc aacctg                                            26
```

METHODS OF SELECTING A DOPAMINERGIC NEURON PROLIFERATIVE PROGENITOR CELLS USING LRP4/CORIN MARKERS

CROSS REFERENCES TO RELATED APPLICATIONS

This application is division of U.S. application Ser. No. 12/110,111 filed Apr. 25, 2008, now U.S. Pat. No. 7,807,371, issued Oct. 5, 2012, which is a division of U.S. application Ser. No. 10/543,003 filed Apr. 24, 2006, now abandoned, which is a U.S. National Phase Application of PCT/JP04/000629, filed Jan. 23, 2004, which claims the benefit of Japanese Application No. 2003-016790, filed Jan. 24, 2003, all of which are herein incorporated by reference in their entirety.

TECHNICAL FIELD

Lrp4 is identified as a gene expressed in dopaminergic neuron progenitor cells prior to cell cycle exit. Dopaminergic neuron progenitor cells that can be used in transplantation therapy for neurodegenerative diseases, such as Parkinson's disease (PD), can be efficiently isolated by detecting the expression of this gene or transmembrane proteins encoded by this gene.

BACKGROUND ART

The dopamine system is an extremely important system for essential motor regulation, hormone secretion regulation, emotion regulation, and such in the mammalian brain. Thus, abnormalities in dopaminergic neural transmission cause various neural disorders. For example, Parkinson's disease (PD) is a neurodegenerative disease of the extrapyramidal system that occurs due to specific degeneration of dopaminergic neurons in the substantia nigra of the midbrain (Harrison's Principles of Internal Medicine, Vol. 2, 23rd edition, Isselbacher et al., ed., McGraw-Hill Inc., NY (1994), pp. 2275-7). Oral administration of L-DOPA (3,4-dihydroxyphenylalanine) is performed as a primary therapeutic method for Parkinson's disease to compensate for the decrease in the amount of dopamine produced; however, the duration of the effect is known to be unsatisfactory.

More recently, a therapeutic method in which the midbrain ventral region of 6 to 9-week old aborted fetuses containing dopaminergic neuron progenitor cells are transplanted to compensate for the loss of dopaminergic neurons was attempted on Parkinson's disease (U.S. Pat. No. 5,690,927; Spencer et al. (1992) N. Engl. J. Med. 327: 1541-8; Freed et al. (1992) N. Engl. J. Med. 327: 1549-55; Widner et al. (1992) N. Engl. J. Med. 327: 1556-63; Kordower et al. (1995) N. Engl. J. Med. 332: 1118-24; Defer et al. (1996) Brain 119: 41-50; Lopez-Lozano et al. (1997) Transp. Proc. 29: 977-80). However, in addition to cell supply and ethical issues (Rosenstain (1995) Exp. Neurol. 33: 106; Turner et al. (1993) Neurosurg. 33: 1031-7), this method is currently under criticism for various other problems, including risk of infection and contamination, immunological rejection of transplants (Lopez-Lozano et al. (1997) Transp. Proc. 29: 977-980; Widner and Brudin (1988) Brain Res. Rev. 13: 287-324), and low survival rates due to fetal tissues' primary dependence on the lipid metabolism rather than glycolysis (Rosenstein (1995) Exp. Neurol. 33: 106).

In order to resolve the ethical issues and shortage of supply, methods have been proposed that use, for example, porcine cortex, stria, and midbrain cells (for example, Published Japanese Translation of International Publication No. Hei 10-508487, Published Japanese Translation of International Publication No. Hei 10-508488 or Published Japanese Translation of International Publication No. Hei 10-509034). In these methods, a complex procedure that involves the alteration of cell surface antigens (MHC class I antigens) is required to suppress rejection. A method involving local immunosuppression by simultaneously transplanting Sertoli's cells has been proposed as a method of eliminating transplant rejection (Published Japanese Translation of International Publication No. Hei 11-509170, Published Japanese Translation of International Publication No. Hei 11-501818, Selawry and Cameron (1993) Cell Transplant 2: 123-9). It is possible to obtain transplant cells from relatives that have matching MHCs, bone marrow from other individuals, bone marrow banks, or umbilical cord-blood banks. However, if it were possible to use the patient's own cells, the problem of rejection reactions could be overcome without any laborious procedures and trouble.

Therefore, the use of dopaminergic neurons differentiated in vitro from non-neural cells such as embryonic stem (ES) cells and bone marrow interstitial cells, instead of cells from aborted fetuses, as transplant materials is considered to be promising. In actuality, functional dopaminergic neurons were reported to have been formed by transplanting ES cells to lesion stria of a rat Parkinson's disease model (Kim et al. (2002) Nature 418: 50-56). It is believed that the importance of regenerative therapy from ES cells or the patient's own nerve stem cells will increase in the future.

In the treatment of damage to nerve tissue, it is necessary to reconstruct brain function, and in order to form a suitable link with surrounding cells (network formation), it is necessary to transplant immature cells, cells capable of differentiating in vivo into neurons. In the transplanting of neuron progenitor cells, in addition to the aforementioned problem regarding supply, there is also the possibility of the progenitor cells differentiating into groups of heterogeneous cells. For example, in treating Parkinson's disease, it is necessary to selectively transplant catecholamine-containing neurons that produce dopamine. Examples of transplant cells that have been proposed in the past for use in the treatment of Parkinson's disease include striatum (Lindvall et al. (1989) Arch. Neurol. 46: 615-31; Widner et al. (1992) N. Engl. J. Med. 327: 1556-63), immortalized cell lines derived from human fetal neurons (Published Japanese Translation of International Publication No. Hei 8-509215; Published Japanese Translation of International Publication No. Hei 11-506930; Published Japanese Translation of International Publication No. 2002-522070), human postmitotic neurons derived from NT2Z cells (Published Japanese Translation of International Publication No. Hei 9-5050554), primordial neuron cells (Published Japanese Translation of International Publication No. Hei 11-509729), cells and bone marrow stroma cells transfected with exogenous genes so as to produce catecholamines such as dopamines (Published Japanese Translation of International Publication No. 2002-504503; Published Japanese Translation of International Publication No. 2002-513545), and genetically engineered ES cells (Kim et al. (2002) Nature 418: 50-56). However, none of these contain only dopaminergic neurons or cells that differentiate into dopaminergic cells.

A method has been proposed for selectively concentrating and isolating dopaminergic neurons from undifferentiated cell populations. In this method, a reporter gene that expresses a fluorescent protein is introduced into each cell of the cell population, under the control of a promoter/enhancer of genes, such as the tyrosine hydroxylase (TH) expressed in dopaminergic neurons, and then cells that emit fluorescence are isolated. The dopaminergic neurons are visualized in their viable state, and concentrated, isolated, and identified (Unexamined Published Japanese Patent Application No. 2002-51775). This method requires the complicated step of introducing an exogenous gene, and further, the presence of a reporter gene poses problems of toxicity and immunogenicity when used in conjunction with gene therapy.

DISCLOSURE OF THE INVENTION

One of the major problems in Parkinson's disease (PD) transplantation therapy at the moment is that both in vitro differentiated dopaminergic neuron precursor cells and midbrain ventral region of aborted fetuses are mixtures of a myriad of cell types. When considering the safety in neural circuit formation, it is preferable to use isolated cells that comprise only the cell type of interest. Furthermore, when considering the risk of tumorigenesis, it is believed that it would be better to use isolated postmitotic neuron. Moreover, when considering the survival of cells at their transplantation site in the brain, and their ability to properly form a network, it is expected that therapeutic effects can be further improved by isolating progenitor cells at as early a stage as possible. Therefore, the inventors of the present invention aimed to isolate a gene specific to dopaminergic neuron progenitor cells. A novel gene 65B13 has already been successfully isolated and applied for patent (Japanese Patent Application No. 2002-307573) as a gene transiently expressed in neuron progenitor cells immediately after cell cycle exit.

In order to isolate genes specific for dopaminergic neuron progenitor cells, a gene specifically expressed in the most ventral region of the E12.5 murine midbrain containing dopaminergic neurons was identified using a modification ("Method for Homogenizing the Amounts of DNA Fragments and Subtraction Method", Japanese Patent Application No. 2001-184757 (filing date: Jun. 19, 2001)) of the subtraction method (N-RDA: Representational Difference Analysis; RDA (Listsyn N. A. (1995) Trends Genet. 11: 303-7) by additionally dividing the ventral region into two regions in the dorsoventral direction. One of the isolated fragments was a cDNA fragment encoding Lrp4/Corin. Lrp4 encodes a type II transmembrane protein (FIG. 1).

As a result of expression analysis by in situ hybridization, Lrp4 was found to be specifically expressed in dopaminergic neuron proliferative progenitor cells in the midbrain (FIGS. 4 and 5). Lrp4 is expressed in the heart from the fetal period to adulthood, and is a type II transmembrane protease which is thought to cleave atrial natriuretic peptides (ANP), a blood pressure-regulating hormone. ANP are expressed as pro-ANP, and, after being secreted outside the cells, are cleaved by Lrp4 on the surface of the cell membrane resulting in active ANP. There have been no previous reports of genes encoding membrane proteins specifically expressed in proliferating dopaminergic neuron progenitor cells. Antibodies to Lrp4 protein expressed on the cell membrane surface are believed to be extremely effective in isolating Lrp4-expressing cells. For example, pure dopaminergic neuron progenitor cells can be obtained by isolating Lrp4-expressing cells from the midbrain ventral region or cultured cells containing dopaminergic neurons differentiated in vitro, using anti-Lrp4 antibodies (FIG. 6).

Moreover, the progenitor cells can be transplanted directly or after having been grown in vitro. The progenitor cells of the present invention also have the potential to differentiate and mature at the optimum location in the brain, as well as the potential to additionally grow in vivo, and can be expected to demonstrate long-term therapeutic effects. In addition, if Lrp4-expressing cells are transplanted after having differentiated and matured in vitro, they can be expected to demonstrate therapeutic effects even if for some reason they do not differentiate into dopaminergic neurons in vivo. In consideration of the risks of tumorigenesis and such, an even higher degree of safety can be expected if cells that have been isolated using a postmitotic neuron marker such as 65B13 after differentiating Lrp4-expressing cells grown in vitro are transplanted. The use of Lrp4-expressing cells for transplantation therapy after being isolated regardless of the method enables a high degree of safety since only the cell type of interest is isolated. In addition, since the earliest progenitor cells can be used, high therapeutic efficacy can be expected in terms of their survival rate, network formation ability, and such. Further, even if the best therapeutic effects cannot be achieved by these early progenitor cells immediately after isolation, since progenitor cells isolated using a marker of the present invention can mature in vitro by culturing or such, materials in the optimum stage of differentiation can be prepared (FIG. 6).

On the other hand, pure dopaminergic neuron progenitor cells are also useful in the search of therapeutic targets for Parkinson's disease, such as for use in the isolation of genes specific to dopaminergic neurons. In particular, being able to obtain proliferative progenitor cells is useful for research on the maturation process of dopaminergic neurons, screening systems using maturation as an index, drug screening in which progenitor cells are grown in vitro or in vivo, screening for drugs that induce differentiation of progenitor cells in vivo (in vivo regenerative therapy drugs), and the like.

More specifically, the present invention relates to:

[1] a dopaminergic neuron proliferative progenitor cell marker polynucleotide probe comprising a sequence selected from the following nucleotide sequences (1) to (5):
  (1) a nucleotide sequence complementary to a nucleotide sequence of SEQ ID NO: 1 or 2;
  (2) a nucleotide sequence complementary to a nucleotide sequence encoding an amino acid sequence of SEQ ID NO: 3 or 4;
  (3) a nucleotide sequence complementary to a nucleotide sequence encoding a sequence lacking a transmembrane domain in an amino acid sequence of SEQ ID NO: 3 or 4;
  (4) a nucleotide sequence that hybridizes under stringent conditions with a polynucleotide consisting of a nucleotide sequence of SEQ ID NO: 1 or 2; and,
  (5) a nucleotide sequence comprising at least 15 contiguous nucleotides selected from sequences of (1) to (4),

[2] an antibody against a polypeptide selected from the following (1) to (6):
  (1) a polypeptide encoded by a nucleotide sequence of SEQ ID NO: 1 or 2;
  (2) a polypeptide comprising an amino acid sequence of SEQ ID NO: 3 or 4;
  (3) a polypeptide comprising an amino acid sequence lacking a transmembrane domain in an amino acid sequence of SEQ ID NO: 3 or 4;
  (4) a polypeptide comprising an amino acid sequence with a deletion, insertion, substitution, or addition of one or more amino acids in an amino acid sequence of SEQ ID NO: 3 or 4;
  (5) a polypeptide encoded by a nucleotide sequence that hybridizes under stringent conditions with a sequence complementary to a nucleotide sequence of SEQ ID NO: 1 or 2; and, (6) a polypeptide that is a fragment of a polypeptide of (1) to (5) comprising at least 8 amino acid residues,

[3] a method of selecting a dopaminergic neuron proliferative progenitor cell, wherein the method comprises the step of contacting the polynucleotide of [1] with a cell sample thought to comprise a dopaminergic neuron progenitor cell,

[4] a method of selecting a dopaminergic neuron proliferative progenitor cell, wherein the method comprises the step of contacting the antibody of [2] with a cell sample thought to comprise a dopaminergic neuron proliferative progenitor cell,

[5] a method of selecting a postmitotic dopaminergic neuron progenitor cell comprising the steps of:
(1) selecting a dopaminergic neuron progenitor cell using the method of [3] or [4];
(2) culturing the proliferative progenitor cell selected in (1); and,
(3) screening the progenitor cell cultured in (2) using a postmitotic dopaminergic neuron marker,

[6] a dopaminergic neuron proliferative progenitor cell selected using the method of [3] or [4],

[7] a postmitotic dopaminergic neuron progenitor cell selected using the method of [5],

[8] a method of isolating a gene specific to a dopaminergic neuron proliferative progenitor cell and a gene specific to each maturation stage of the progenitor cell differentiating into a dopaminergic neuron, wherein the method comprises the step of detecting and isolating a gene specifically expressed in the proliferative progenitor cell of [6], or a cell differentiated, induced, or proliferated from the progenitor cell, and

[9] a method of screening using maturation as an index, wherein the method comprises the steps of contacting a test substance with the proliferative progenitor cell of [6], and detecting the differentiation or proliferation of the progenitor cell induced by the contact.

<Marker Polynucleotide Probes>

The dopaminergic neuron proliferative progenitor cell marker polynucleotide probes of the present invention are used as markers that select and/or detect dopaminergic neuron progenitor cells. Polynucleotides used for this probe comprise a nucleotide sequence complementary to the nucleotide sequence of SEQ ID NO: 1 or 2 encoding Lrp4 polypeptide expressed in dopaminergic neuron progenitor cells prior to cell cycle exit. SEQ ID NO: 1 is the nucleotide sequence of murine Lrp4 cDNA, SEQ ID NO: 2 is the nucleotide sequence of human Lrp4 cDNA, and both sequences have been registered in GenBank (murine: Accession No. NM 016869; human: Accession No. XM 035037).

Here, a "marker polynucleotide probe" refers to a polymer composed of a number of nucleotides, such as deoxyribonucleic acids (DNAs) or ribonucleic acids (RNAs), or nucleotide pairs, that should be able to detect expression of Lrp4, particularly transcribed mRNA. Double-stranded cDNA is also known to be able to be used as a probe in tissue in situ hybridization, and such double-stranded cDNA is included in the marker of the present invention. RNA probes (riboprobes) are particularly preferable as marker polynucleotide probes for detecting RNA in tissue. If needed, the marker polynucleotide probes of the present invention can also contain non-naturally-occurring nucleotides such as 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueuosine, 5-methoxycarbonylmethyl-2-thiouridine, 5-methoxycarbonylmethyluridine, 5-methoxyuridine, 2-methylthio-N6-isopentenyladenosine, N-((9-β-D-ribofuranosyl-2-methylthiopurin-6-yl)carbamoyl)threonine, N-((9-β-D-ribofuranosylpurin-6-yl)N-methylcarbamoyl)threonine, uridine-5-oxyacetic acid-methyl ester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-β-D-ribofuranosylpurin-6-yl)carbamoyl)threonine, 2'-O-methyl-5-methyluridine, 2'-O-methyluridine, wybutosine, and 3-(3-amino-3-carboxy propyl)uridine.

Moreover, a marker polynucleotide probe of the present invention comprises a nucleotide sequence complementary to a nucleotide sequence encoding the amino acid sequence of SEQ ID NO: 3 or 4 that encodes Lrp4 polypeptide specifically expressed in dopaminergic neuron progenitor cells prior to cell cycle exit. The nucleotide sequence that encodes the amino acid sequence of SEQ ID NO: 3 or 4 includes not only nucleotide sequences of SEQ ID NO: 1 or 2, but also nucleotide sequences that differ from the sequence of SEQ ID NO: 1 or 2 due to degeneracy of the genetic code. The marker polynucleotide probes of the present invention also include those which comprise a sequence complementary to the nucleotide sequence encoding a sequence that lacks a transmembrane domain in the amino acid sequence of SEQ ID NO: 3 or 4. There is no signal sequence in the amino acid sequence of SEQ ID NO: 3 or 4. In murine Lrp4 (SEQ ID NO: 3), amino acid residues 113-135 form a transmembrane domain, while in human Lrp4 (SEQ ID NO: 4), amino acid residues 46-68 form a transmembrane domain. Furthermore, the sequences described in SEQ ID NOs: 3 and 4 are respectively registered in GenBank.

Herein, the phrase "complementary to a nucleotide sequence" encompasses not only cases wherein a nucleotide sequence completely pairs with the template, but also includes those that have at least 70%, preferably 80%, more preferably 90%, and even more preferably 95% or more (for example, 97% or 99%) of the nucleotides paired with the template. To pair refers to the formation of a chain, in which T (U in the case of an RNA) corresponds to A, A corresponds to T or U, G corresponds to C, and C corresponds to G in the nucleotide sequence of the template polynucleotide. Homologies at the nucleotide sequence level between certain polynucleotides can be determined by the BLAST algorithm (Altschul (1990) Proc. Natl. Acad. Sci. USA 87: 2264-8; Karlin and Altschul (1993) Proc. Natl. Acad. Sci. USA 90: 5873-7). The BLASTN program for nucleotide sequences (Altschul et al. (1990) J. Mol. Biol. 215: 403-410) has been developed based on this algorithm, and can be used to determine the homology of marker polynucleotide probe sequences (see on the world wide web at ncbi.nlm.nih.gov for a specific example of analysis methods).

Moreover, a marker polynucleotide probe of the present invention includes a polynucleotide that contains a sequence that hybridizes under stringent conditions with a polynucleotide comprised of the nucleotide sequence of SEQ ID NO: 1 or 2 that encodes Lrp4 polypeptide specifically expressed in dopaminergic neuron progenitor cells prior to cell cycle exit. Although polynucleotides that have a nucleotide sequence indicated in SEQ ID NO: 1 or 2 are known with respect to Lrp4, their alternative isoforms and allelic variants may also exist. Polynucleotides having a sequence complementary to such isoforms and allelic variants can also be used as a marker polypeptide of the present invention. Such isoforms and allelic variants can be obtained from cDNA libraries or genomic libraries derived from animals such as humans, mice, rats, rabbits, hamsters, chickens, pigs, cows, goats, and sheep, by using a polynucleotide probe comprising a nucleotide sequence of SEQ ID NO: 1 or SEQ ID NO: 2, in known hybridization methods, such as colony hybridization, plaque hybridization, or Southern blotting. See "Molecular Cloning, A Laboratory Manual 2nd ed." (Cold Spring Harbor Press (1989)) for methods of cDNA library construction. In addition, a commercially available cDNA library or genomic library may also be used.

More specifically, in constructing a cDNA library, total RNA is first prepared from cells, organs, tissues, or such that express Lrp4, by known techniques, such as guanidine ultracentrifugation (Chirwin et al. (1979) Biochemistry 18: 5294-5299) or AGPC (Chomczynski and Sacchi (1987) Anal. Biochem. 162: 156-159), followed by purification of mRNA using the mRNA Purification Kit (Pharmacia), or such. A kit for direct mRNA preparation, such as the QuickPrep mRNA Purification Kit (Pharmacia), may also be used. Next, cDNA is synthesized from the resulting mRNA using reverse transcriptase. cDNA synthesis kits, such as the AMV Reverse Transcriptase First-strand cDNA Synthesis Kit (Seikagaku Corporation), are also commercially available. Other methods that use the 5'-RACE method to synthesize and amplify cDNA by PCR may also be used (Frohman et al. (1988) Proc. Natl. Acad. Sci. USA 85: 8998-9002; Belyaysky et al. (1989) Nucleic Acids Res. 17: 2919-32). In addition, in order to construct cDNA libraries containing a high percentage of full-length clones, known techniques such as the oligo-capping method (Maruyama and Sugano (1994) Gene 138: 171-4; Suzuki (1997) Gene 200: 149-56) can also be employed. The cDNA obtained in this manner is then incorporated into a suitable vector.

Examples of hybridization conditions suitable for use in the present invention include "2×SSC, 0.1% SDS, 50° C.", "2×SSC, 0.1% SDS, 42° C." and "1×SSC, 0.1% SDS, 37° C.". Examples of conditions of higher stringency include "2×SSC, 0.1% SDS, 65° C.", "0.5×SSC, 0.1% SDS, 42° C." and "0.2× SSC, 0.1% SDS, 65° C.". More specifically, a method that uses the Rapid-hyb buffer (Amersham Life Science) can be carried out by performing pre-hybridization at 68° C. for 30 minutes or more, adding a probe to allow hybrid formation at 68° C. for 1 hour or more, washing three times in 2×SSC/0.1% SDS at room temperature for 20 minutes each, washing three times in 1×SSC/0.1% SDS at 37° C. for 20 minutes each, and finally washing twice in 1×SSC/0.1% SDS at 50° C. for 20 minutes each. This can also be carried out using, for example, the Expresshyb Hybridization Solution (CLONTECH), by performing pre-hybridization at 55° C. for 30 minutes or more, adding a labeled probe and incubating at 37° C. to 55° C. for 1 hour or more, washing three times in 2×SSC/0.1% SDS at room temperature for 20 minutes each, and washing once at 37° C. for 20 minutes with 1×SSC/0.1% SDS. Herein, conditions of higher stringency can be achieved by increasing the temperature for pre-hybridization, hybridization, or second wash. For example, a pre-hybridization and hybridization temperature of 60° C. can be raised to 68° C. for higher stringency. In addition to factors such as salt concentration of the buffer and temperature, a person with ordinary skill in the art can also integrate other factors, such as probe concentration, probe length, and reaction time, to obtain Lrp4 isoforms and allelic variants, and corresponding genes derived from other organisms.

References such as Molecular Cloning, A Laboratory Manual $2^{nd}$ ed. (Cold Spring Harbor Press (1989); Section 9.47-9.58), Current Protocols in Molecular Biology (John Wiley & Sons (1987-1997); Section 6.3-6.4), DNA Cloning 1: Core Techniques, A Practical Approach $2^{nd}$ ed. (Oxford University (1995); Section 2.10 for conditions, in particular), can be referred to for detailed information on hybridization procedures. Examples of hybridizing polynucleotides include polynucleotides containing a nucleotide sequence that has at least 50% or more, preferably 70%, more preferably 80% and even more preferably 90% (for example, 95% or more, or 99%) identity with a nucleotide sequence comprising the nucleotides of SEQ ID NO: 1 or SEQ ID NO: 2. Such identities can be determined by the BLAST algorithm (Altschul (1990) Proc. Natl. Acad. Sci. USA 87: 2264-8; Karlin and Altschul (1993) Proc. Natl. Acad. Sci. USA 90: 5873-7) as described in the homology determination above. In addition to the above-described BLASTN program for nucleotide sequences, the BLASTX program for determining the identity of amino acid sequences (Altschul et al. (1990) J. Mol. Biol. 215: 403-10) and the like have been developed based on this algorithm and can be used (as described above, see on the world wide web at ncbi.nlm.nih.gov. for a specific example of analysis methods).

Lrp4 isoforms or allelic variants, and other genes with an Lrp4-like structure or function, can be obtained from cDNA libraries and genomic libraries of animals such as humans, mice, rats, rabbits, hamsters, chickens, pigs, cows, goats, and sheep, by designing primers based on the nucleotide sequences of SEQ ID NOs: 1 and 2, using gene amplification technology (PCR) (Current Protocols in Molecular Biology, John Wiley & Sons (1987) Sections 6.1-6.4).

The polynucleotide sequences can be confirmed by using conventional sequence determination methods. For example, the dideoxynucleotide chain termination method (Sanger et al. (1977) Proc. Natl. Acad. Sci. USA 74: 5463) can be used. In addition, sequences can also be analyzed using a suitable DNA sequencer.

Moreover, a marker polynucleotide probe of the present invention includes the aforementioned (1) sequence complementary to the nucleotide sequence of SEQ ID NO: 1 or 2, (2) sequence complementary to a nucleotide sequence that encodes the amino acid sequence described in SEQ ID NO: 3 or 4, (3) sequence complementary to a nucleotide sequence that encodes a sequence lacking the transmembrane domain portion of the amino acid sequence described in SEQ ID NO: 3 or 4, and (4) polynucleotide comprising a nucleotide sequence that contains at least 15 consecutive nucleotides in each of the nucleotide sequences that hybridize under stringent conditions with a polynucleotide comprised of the nucleotide sequence of SEQ ID NO: 1 or 2.

Such a polynucleotide comprising a nucleotide sequence that contains at least 15 consecutive nucleotides can be used as a probe for detecting, or as a primer for amplifying, the expression of Lrp4 mRNA. The nucleotide chain normally consists of 15 to 100, and preferably 15 to 35 nucleotides when used as a probe, or at least 15 and preferably 30 nucleotides when used as a primer. A primer can be designed to have a restriction enzyme recognition sequence, a tag or such, added to the 5'-end side thereof, and at the 3' end, a sequence complementary to a target sequence. Such a polynucleotide, comprising a nucleotide sequence that contains at lease 15 consecutive nucleotides, can hybridize with an Lrp4 polynucleotide.

A marker polynucleotide probe of the present invention can be prepared by the aforementioned hybridization or PCR or such from cells that express Lrp4. In addition, a marker polynucleotide probe of the present invention can also be produced by chemical synthesis based on known Lrp4 sequence data. Riboprobes, which are considered to be particularly preferable for detecting RNA in tissue, can be obtained by, for example, inserting a cloned Lrp4 gene or portion thereof into plasmid vector pSP64 in the reverse direction followed by run-off transcription of the inserted sequence portion. Although pSP64 contains an SP6 promoter, methods for producing riboprobes by combining phage T3, T7 promoter and RNA polymerase are also known.

<Antibodies>

The present invention also provides antibodies that can be used to select dopaminergic neuron progenitor cells from brain tissue or cultured cells. Antibodies of the present invention include polyclonal antibodies, monoclonal antibodies, chimeric antibodies, single-chain antibodies (scFV) (Huston et al. (1988) Proc. Natl. Acad. Sci. USA 85: 5879-83; The Pharmacology of Monoclonal Antibody, vol. 113, Rosenburg and Moore ed., Springer Verlag (1994) pp. 269-315), humanized antibodies, multispecific antibodies (LeDoussal et al. (1992) Int. J. Cancer Suppl. 7: 58-62; Paulus (1985) Behring Inst. Mitt. 78: 118-32; Millstein and Cuello (1983) Nature 305: 537-9; Zimmermann (1986) Rev. Physiol. Biochem. Pharmacol. 105: 176-260; Van Dijk et al. (1989) Int. J. Cancer 43: 944-9), and antibody fragments such as Fab, Fab', F(ab')2, Fc, and Fv. Moreover, an antibody of the present invention may also be modified by PEG and such, as necessary. An antibody of the present invention may also be produced in the form of a fusion protein with β-galactosidase, maltose-binding protein, GST, green fluorescent protein (GFP) and such, to allow detection without the use of a secondary antibody. In addition, an antibody may be modified by labeling with biotin or such, to allow recovery using avidin, streptoavidin, or such.

The antibodies of present invention are specific to any of (1) a polypeptide encoded by the nucleotide sequence of SEQ ID NO: 1 or 2, (2) a polypeptide comprised of the amino acid sequence described in SEQ ID NO: 3 or 4, (3) a polypeptide comprised of an amino acid sequence lacking a transmembrane domain in the amino acid sequence described in SEQ ID NO: 3 or 4, (4) a polypeptide comprised of an amino acid sequence wherein one or more amino acids in the amino acid sequence of SEQ ID NO: 3 or 4 are deleted, inserted, substituted, or added, (5) a polypeptide encoded by a nucleotide sequence that hybridizes under stringent conditions with a sequence complementary to the nucleotide sequence of SEQ ID NO: 1 or 2, and (6) a polypeptide that is a fragment of a polypeptide of (1) to (5) above that has at least eight amino acid residues.

An antibody of the present invention can be produced using as a sensitizing antigen an Lrp4 polypeptide, or a fragment thereof, or cells that express Lrp4 polypeptide or Lrp4 polypeptide fragment. In addition, a short fragment of Lrp4 polypeptide may also be used as an immunogen by coupling to a carrier such as bovine serum albumin, Keyhole-limpet hemocyanin, and ovalbumin. In addition, the Lrp4 polypeptide, or a fragment thereof, may be used in combination with a known adjuvant, such as aluminum adjuvant, Freund's complete (or incomplete) adjuvant, or pertussis adjuvant, to enhance the immune response to the antigen.

The "Lrp4 polypeptide" in the present invention is a peptide polymer, a preferred example of which is a protein having the amino acid sequence described in SEQ ID NO: 3 or 4. The amino acid residues that compose an Lrp4 polypeptide may be naturally occurring or modified ones. Moreover, the Lrp4 polypeptides include proteins lacking a transmembrane domain portion, and fusion proteins modified by other peptide sequences.

In the present invention, the Lrp4 polypeptide should have the antigenicity of an Lrp4 polypeptide, and includes a polypeptide having an amino acid sequence wherein one or more amino acids in the amino acid sequence of SEQ ID NO: 3 or 4 are deleted, inserted, substituted, or added. It is well known that mutant polypeptides comprising an amino acid sequence in which one or more amino acids are deleted, inserted, substituted, or added, maintain the same biological activity as the original polypeptide (Mark et al. (1984) Proc. Natl. Acad. Sci. USA 81: 5662-6; Zoller and Smith (1982) Nucleic Acids Res. 10: 6487-500; Wang et al. (1984) Science 224: 1431-3; Dalbadie-McFarland et al. (1982) Proc. Natl. Acad. Sci. USA 79: 6409-13). Such a polypeptide that maintains the antigenicity of Lrp4 and having an amino acid sequence in which one or more amino acids are deleted, inserted, substituted, or added to the amino acid sequence of SEQ ID NO: 3 or 4, can be obtained by preparing a polynucleotide that encodes the polypeptide according to known methods such as site-directed mutagenesis described in "Molecular Cloning, A Laboratory Manual 2nd ed." (Cold Spring Harbor Press (1989)), "Current Protocols in Molecular Biology" (John Wiley & Sons (1987-1997); especially section 8.1-8.5), Hashimoto-Goto et al. (1995) Gene 152: 271-5, Kunkel (1985) Proc. Natl. Acad. Sci. USA 82: 488-92, Kramer and Fritz (1987) Method. Enzymol. 154: 350-67, Kunkel (1988) Method. Enzymol. 85: 2763-6), and others, and then suitably expressing.

An Lrp4 polypeptide fragment is identical to a portion of the aforementioned Lrp4 polypeptide, and consists of at least eight amino acid residues or more (for example, 8, 10, 12, or 15 amino acid residues or more). A particularly preferred fragment can be exemplified by a polypeptide fragment lacking an amino terminus, carboxyl terminus, and transmembrane domain. The Lrp4 polypeptide fragments include fragments containing an α-helix and α-helix forming region, α-amphipathic region, β-sheet and β-sheet forming region, β-amphipathic region, substrate binding region, high antigen index region, coil and coil forming region, hydrophilic region, hydrophobic region, turn and turn forming region, and surface forming region. In the context of the present invention, an Lrp4 polypeptide fragment may be any fragment, so long as it has the antigenicity of an Lrp4 polypeptide. The antigen-determining site of a polypeptide can be predicted by using methods for analyzing hydrophobicity/hydrophilicity of an amino acid sequence of a protein (Kyte-Doolittle (1982) J. Mol. Biol. 157: 105-22), or methods of secondary structure analysis (Chou-Fasman (1978) Ann. Rev. Biochem. 47: 251-76), and can be confirmed using a computer program (Anal. Biochem. 151: 540-6 (1985)), or the PEPSCAN method in which a short peptide is synthesized followed by confirmation of its antigenicity (Published Japanese Translation of International Publication No. Sho 60-500684), or the like.

Lrp4 polypeptides and Lrp4 polypeptide fragments can be isolated from Lrp4-expressing cells, tissues, etc., based on their physical properties and such. In addition, these polypeptides and polypeptide fragments can also be produced using known genetic recombination techniques or chemical synthesis methods. For example, for in vitro Lrp4 polypeptide production, Lrp4 polypeptides can be produced in an in vitro cell-free system using methods such as in vitro translation (Dasso and Jackson (1989) Nucleic Acids Res. 17: 3129-44). In contrast, when producing polypeptides using cells, a polynucleotide that encodes a polypeptide of interest is first incorporated into an appropriate vector, a suitable cell host is selected, and then the cells are transformed by the vector. Subsequently, the transformed cells can be cultured to obtain a polypeptide of interest.

Appropriate vectors include various vectors, such as plasmids, cosmids, viruses, bacteriophages, cloning vectors, and expression vectors (Molecular Cloning, A Laboratory Manual $2^{nd}$ ed., Cold Spring Harbor Press (1989); Current Protocols in Molecular Biology, John Wiley & Sons (1987)). Vectors comprise regulatory sequences for the expression of a desired polynucleotide in transfected host cells, and the polynucleotide is incorporated therein so that it will be under the control of the regulatory sequences. Here, the phrase "regulatory sequence" includes promoters, ribosome binding sites, and terminators in the case of a prokaryotic host cell, and promoters and terminators in the case of a eukaryotic host cell, and in some cases, may also contain transactivators, transcription factors, poly A signals which stabilize transcription products, splicing and polyadenylation signals, and others. Such a regulatory sequence comprises all the components required for the expression of a polynucleotide linked thereto. A vector may further comprise a selection marker. Moreover, a signal peptide required for transferring an intracellularily expressed polypeptide into the lumen of the endoplasmic reticulum, or the periplasm or extracellular space when the host is a Gram negative microbe, can also be incorporated into an expression vector by linking to a polypeptide of interest. Such a signal peptide can be a signal peptide derived from a heterogeneous protein. Moreover, a linker may be added, and a start (ATG) or stop codon (TAA, TAG, or TGA) may be inserted as necessary.

Examples of vectors capable of expressing polypeptides in vitro include pBEST (Promega). In addition, various vectors are known to be suitable for expression in prokaryotic hosts (see, e.g., "Basic Microbiology Course 8—Genetic Engineering" (Kyoritsu Publishing)). When selecting prokaryotic cells as the host, a person with ordinary skill in the art can suitably select a vector suitable for the host and a suitable method for introducing the vector into the host. Other examples of hosts that can be used to express Lrp4 polypeptides and their antigenic fragments include fungal cells such as yeasts, higher plants, insects, fish, amphibians, reptiles, birds, mammals, cultured cells (COS, Hela, C127, 3T3, BHK, HEK293, Bowes melanoma cells), myeloma, Vero, Namalwa, Namalwa KJM-1, and HBT5637 (Unexamined Published Japanese Patent Application No. Sho 63-299). Vector systems suitable for each cell and methods for introducing a vector into host cells are also known. Moreover, methods for expressing exogenous proteins in animals in vivo (see, e.g., Susumu (1985) Nature 315: 592-4; Lubon (1998) Biotechnol. Annu. Rev. 4: 1-54) and in plant bodies are also known, and can be used to express Lrp4 polynucleotides.

Insertion of a DNA into a vector can be carried in a ligase reaction using restriction enzyme sites (Current Protocols in Molecular Biology, John Wiley & Sons (1987) Section 11.4-11.11; Molecular Cloning, A Laboratory Manual 2nd ed., Cold Spring Harbor Press (1989) Section 5.61-5.63). In addition, an Lrp4 polypeptide-encoding expression vector can be designed as necessary by selecting a nucleotide sequence that has a high expression efficiency in view of the host's codon usage frequency (Grantham et al. (1981) Nucleic Acids Res. 9: r43-74). A host that produces an Lrp4 polypeptide comprises in its cells a polynucleotide that encodes an Lrp4 polypeptide. So long as the polynucleotide does not exist at a naturally occurring position in the genome of a host cell, the polynucleotide itself may be regulated by its own promoter, incorporated in the host genome, or maintained as an extrachromosomal structure.

Culturing of host cells is carried out using known methods that are appropriate for the host cell selected. For example, when animal cells are selected, culturing can be carried out at a pH of about 6 to 8 and a temperature of 30° C. to 40° C. for about 15 to 200 hours, using a medium such as DMEM (Virology 8: 396 (1959)), MEM (Science 122: 501 (1952)), RPMI1640 (J. Am. Med. Assoc. 199: 519 (1967)), 199 (Proc. Soc. Biol. Med. 73: 1 (1950)), or IMDM, and adding serum such as fetal calf serum (FCS), as necessary. In addition, the medium may be replaced, aerated, or stirred, during the course of culturing, as necessary.

Normally, an Lrp4 polypeptide produced by gene recombination techniques can be recovered from the medium if the polypeptide is secreted outside of a cell, or from the body fluid of a transgenic organism. When a polypeptide is produced inside of a cell, the cells are dissolved and the polypeptide is recovered from the dissolved product. The polypeptide of interest is then purified by suitably combining known methods of protein purification, such as salting out, distillation, various types of chromatography, gel electrophoresis, gel filtration, ultrafiltration, recrystallization, acid extraction, dialysis, immunoprecipitation, solvent precipitation, solvent extraction, and ammonium sulfate or ethanol precipitation. Examples of chromatographies include ion exchange chromatography, such as anion or cation exchange chromatography, affinity chromatography, reversed-phase chromatography, adsorption chromatography, gel filtration chromatography, hydrophobic chromatography, hydroxyapatite chromatography, phosphocellulose chromatography, and lectin chromatography (Strategies for Protein Purification and Characterization: A Laboratory Course Manual, Marshak et al. ed., Cold Spring Harbor Laboratory Press (1996)). Chromatography can be carried out using a liquid phase chromatography, such as HPLC or FPLC. In addition, for example, a protein fused with GST can be purified by glutathione column, and a protein with histidine tag can be purified by nickel column. When an Lrp4 polypeptide is produced as a fusion protein, unnecessary portions can be removed using thrombin, factor Xa, or the like, following purification as necessary.

In addition, naturally-occurring polypeptides can also be purified and obtained. For example, polypeptides can be purified by affinity chromatography using antibodies against the Lrp4 polypeptides (Current Protocols in Molecular Biology, John Wiley & Sons (1987) Section 16.1-16.19). Moreover, the purified polypeptide can also be modified using enzymes, such as chymotrypsin, glucosidase, trypsin, protein kinase, and lysyl endopeptidase, as necessary. In addition to the aforementioned synthesis and genetic engineering techniques as used for an Lrp4 polypeptide, an Lrp4 polypeptide fragment can also be produced by cleaving an Lrp4 polypeptide, using suitable enzymes, such as peptidase.

Polyclonal antibodies for selecting dopaminergic neuron proliferative progenitor cells can be obtained from, for example, the serum of an immunized animal after immunizing a mammal with an Lrp4 polypeptide purified as described above, or a fragment thereof, coupled to a desired adjuvant. Although there are no particular limitations on the mammals used, typical examples include rodents, lagomorphs, and primates. Specific examples include rodents such as mice, rats, and hamsters, lagomorphs such as rabbits, and primates such as monkeys, including cynomolgus monkeys, rhesus monkeys, baboons, and chimpanzees. Animal immunization is carried out by suitably diluting and suspending a sensitizing antigen in phosphate-buffered saline (PBS) or physiological saline, mixing with an adjuvant as necessary until emulsified, and injecting into an animal intraperitoneally or subcutaneously. The sensitizing antigen mixed with Freund's incomplete adjuvant is preferably administered several times, every 4 to 21 days. Antibody production can be confirmed by measuring the level of an antibody of interest in the serum using conventional methods. Finally, the serum itself may be used as a polyclonal antibody, or it may be further purified. See, for example, "Current Protocols in Molecular Biology" (John Wiley & Sons (1987) Sections 11.12-11.13), for specific methods.

A monoclonal antibody can be produced by removing the spleen from an animal immunized in the manner described above, separating immunocytes from the spleen, and fusing with a suitable myeloma cell using polyethylene glycol (PEG) or such to establish hybridomas. Cell fusion can be carried out according to the Milstein method (Galfre and Milstein (1981) Methods Enzymol. 73: 3-46). Here, suitable myeloma cells are exemplified particularly by cells that allow chemical selection of fused cells. When using such myeloma cells, fused hybridomas are selected by culturing in a culture medium (HAT culture medium) that contains hypoxanthine, aminopterin, and thymidine, which destroy cells other than the fused cells. Next, a clone that produces an antibody against a polypeptide of the present invention, or a fragment thereof, is selected from the established hybridomas. Subsequently, the selected clone is introduced into the abdominal cavity of a mouse or such, and ascites is collected to obtain a monoclonal antibody. See, in addition, "Current Protocols in Molecular Biology" (John Wiley & Sons (1987) Section 11.4-11.11), for information on specific methods.

Hybridomas can also be obtained by first sensitizing human lymphocytes that have been infected by EB virus with an immunogen in vitro, and fusing the sensitized lymphocytes with human myeloma cells (such as U266) to obtain hybridomas that produce human antibodies (Unexamined Published Japanese Patent Application No. Sho 63-17688). In addition, human antibodies can also be obtained by using antibody-producing cells generated by sensitizing a transgenic animal with a human antibody gene repertoire (WO92/03918; WO93-02227; WO94/02602; WO94/25585; WO96/33735; WO96/34096; Mendez et al. (1997) Nat. Genet. 15: 146-156, etc.). Methods that do not use hybridomas can be exemplified by a method in which a cancer gene is introduced to immortalize immunocytes such as antibody producing lymphocytes.

In addition, antibodies can also be produced by genetic recombination techniques (see Borrebaeck and Larrick (1990) Therapeutic Monoclonal Antibodies, MacMillan Publishers Ltd., UK). First, a gene that encodes an antibody is cloned from hybridomas or antibody-producing cells (such as sensitized lymphocytes). The resulting gene is then inserted into a suitable vector, the vector is introduced into a host, and the host is then cultured to produce the antibody. This type of recombinant antibody is also included in the antibodies of the present invention. Typical examples of recombinant antibodies include chimeric antibodies, comprising a non-human antibody-derived variable region and a human antibody-derived constant region, and humanized antibodies, comprising a non-human-derived antibody complementarity determining region (CDR), human antibody-derived framework region (FR), and human antibody constant region (Jones et al. (1986) Nature 321: 522-5; Reichmann et al. (1988) Nature 332: 323-9; Presta (1992) Curr. Op. Struct. Biol. 2: 593-6; Methods Enzymol. 203: 99-121 (1991)).

Antibody fragments can be produced by treating the aforementioned polyclonal or monoclonal antibodies with enzymes such as papain or pepsin. Alternatively, an antibody fragment can be produced by genetic engineering techniques using a gene that encodes an antibody fragment (see Co et al., (1994) J. Immunol. 152: 2968-76; Better and Horwitz (1989) Methods Enzymol. 178: 476-96; Pluckthun and Skerra (1989) Methods Enzymol. 178: 497-515; Lamoyi (1986) Methods Enzymol. 121: 652-63; Rousseaux et al. (1986) 121: 663-9; Bird and Walker (1991) Trends Biotechnol. 9: 132-7).

Multispecific antibodies include bispecific antibodies (BsAb), diabodies (Db), and such. Multispecific antibodies can be produced by methods such as (1) chemically coupling antibodies having different specificities with different types of bifunctional linkers (Paulus (1985) Behring Inst. Mill. 78: 118-32), (2) fusing hybridomas that secrete different monoclonal antibodies (Millstein and Cuello (1983) Nature 305: 537-9), or (3) transfecting eukaryotic cell expression systems, such as mouse myeloma cells, with a light chain gene and a heavy chain gene of different monoclonal antibodies (four types of DNA), followed by the isolation of a bispecific monovalent portion (Zimmermann (1986) Rev. Physio. Biochem. Pharmacol. 105: 176-260; Van Dijk et al. (1989) Int. J. Cancer 43: 944-9). On the other hand, diabodies are dimer antibody fragments comprising two bivalent polypeptide chains that can be constructed by gene fusion. These can be produced using known methods (see Holliger et al. (1993) Proc. Natl. Acad. Sci. USA 90: 6444-8; EP404097; WO93/11161).

Recovery and purification of antibodies and antibody fragments can be carried out using Protein A and Protein G, or according to the protein purification techniques as described above in producing nonantibody polypeptides (Antibodies: A Laboratory Manual, Ed Harlow and David Lane, Cold Spring Harbor Laboratory (1988)). For example, when using Protein A to purify an antibody of the present invention, known Protein A columns such as Hyper D™, POROS™, or Sepharose F.F.™ (Pharmacia) can be used. The concentration of the resulting antibody can be determined by measuring the absorbance or by enzyme linked immunoadsorbent assay (ELISA).

Antigen binding activity of an antibody can be determined by absorbance measurement, or by using fluorescent antibody methods, enzyme immunoassay (EIA) methods, radioimmunoassay (RIA) methods, or ELISA, When ELISA is used, an antibody of the present invention is first immobilized onto a support, such as a plate. An Lrp4 polypeptide is added, and then a sample containing the antibody of interest is added. Herein, samples containing an antibody of interest include, for example, culture supernatants of antibody-producing cells, purified antibodies, and such. Next, a secondary antibody that recognizes an antibody of the present invention is added, followed by the incubation of the plate. Subsequently, the plate is washed and the label attached to the secondary antibody is detected. Namely, if a secondary antibody is labeled with alkaline phosphatase, the antigen binding activity can be determined by adding an enzyme substrate such as p-nitrophenyl phosphate, and measuring the absorbance. In addition, a commercially available system such as BIAcore™ (Pharmacia) can also be used to evaluate antibody activities.

<Selection of Dopaminergic Neurons>

The present invention provides a method of selectively obtaining homogeneous populations of dopaminergic neuron proliferative progenitor cells prior to cell cycle exit. Dopaminergic neuron progenitor cells prior to cell cycle exit can be selected using a marker polynucleotide probe or antibody of the present invention. Here, the term "selected" includes both the detection of the presence of dopaminergic neuron proliferative progenitor cells in a sample, and the subsequent separation or isolation of those progenitor cells following the detection of their presence. More specifically, the present invention provides a method of selecting dopaminergic neuron progenitor cells, comprising a step of contacting a marker polynucleotide probe of the present invention with a cell sample containing potential dopaminergic neuron proliferative progenitor cells. In this method, the marker polynucleotide probe is preferably labeled with a radioactive isotope or non-radioactive compound. Examples of radioactive isotopes used for labeling include $^{35}$S and $^{3}$H. When using a radiolabeled marker polynucleotide probe, RNA that binds with the marker can be detected by detecting silver particles using emulsion autoradiography. In addition, examples of non-radioactive isotopes for labeling a marker polynucleotide probe include biotin and digoxigenin. A biotin-labeled marker can be detected using, for example, avidin labeled with fluorescence or an enzyme such as alkaline phosphatase or horseradish peroxidase. On the other hand, anti-digoxigenin antibodies labeled with fluorescence or an enzyme, such as alkaline phosphatase or horseradish peroxidase, can be used to detect a digoxigenin-labeled marker. When using enzyme labeling, detection is carried out by incubating with the enzyme substrate to form a stable pigment at the location of the marker. Fluorescent in situ hybridization (FISH) is convenient and particularly preferable.

In addition, the present invention provides a method of selecting dopaminergic neurons comprising a step of contacting an antibody for selecting dopaminergic neuron proliferative progenitor cells of the present invention with a cell sample containing potential dopaminergic neuron proliferative progenitor cells. Namely, cells expressing Lrp4 polypeptide, or in other words, dopaminergic neuron proliferative progenitor cells prior to cell cycle exit, can be acquired by contacting a cell sample containing potential dopaminergic neuron proliferative progenitor cells with an antibody of the present invention, and selecting those cells that have bound to the antibody (see FIG. 6). The antibody may also be immobilized on a suitable support, prior to cellular contact. Alternatively, cells that bind with the antibody can be selectively recovered, by contacting cells with an antibody and allowing them to bind, and purifying the antibody by affinity chromatography. For example, if an antibody of the present invention is conjugated to biotin, it can be purified on a plate or column bound with avidin or streptoavidin. In addition, magnetic particles can be bound to an antibody, for example, and the antibody and cells that express on their surfaces Lrp4 bound to the antibody, can be recovered using a magnet. Dopaminergic neuron proliferative progenitor cells that express Lrp4 can be selected by flow cytometry using a cell sorter and fluorescent-labeled anti-Lrp4 antibodies and such.

Moreover, the present invention can provide dopaminergic neuron progenitor cells which have a lower risk of tumorigenesis and therefore particularly suitable for transplantation therapy, by screening the cultured progenitor cells using a postmitotic neuron marker after culturing dopaminergic neuron proliferative progenitor cells selected using a marker polynucleotide probe or antibody of the present invention. An example of postmitotic neuron markers is 65B13. For example, dopaminergic neuron precursor cells immediately after cell cycle exit can be selected by contacting antibodies to 65B13 polypeptide with cultured dopaminergic neuron progenitor cells, and selecting those cells that express 65B13 polypeptide. In addition, 65B13 has an Ig domain adhesion molecule-like structure. When 65B13 has been expressed in cultured cells, although cells that have expressed 65B13 adhere together, they do not adhere to cells that do not express 65B13. Consequently, adhesion mediated by 65B13 is considered to involve homophilic binding. Therefore, 65B13-expressing dopaminergic neuron precursor cells can also be screened using the adhesion of the extracellular domain of 65B13 polypeptide.

In addition, Lrp4-expressing dopaminergic neuron proliferative progenitor cells and 65B13-expressing dopaminergic neuron precursor cells can also be selected and/or screened using promoters for Lrp4 and 65B13, respectively (see, for example, Unexamined Published Japanese Patent Application No. 2002-51775). For example, a vector harboring a construct that comprises a gene encoding a detection marker, such as GFP, linked to a promoter region obtained from analyzing the Lrp4 expression regulatory regions to be described later, can be transfected into cells. In addition, a gene encoding a marker can also be knocked in at the Lrp4 gene locus. In either case, specific cells can be selected by detecting the expression of a marker gene specific for dopaminergic neuron progenitor cells. With respect to 65B13, screening can also be performed in a similar manner to Lrp4. For example, the sequence disclosed in Japanese Patent Application No. 2002-307573 can be referred to for 65B13.

The cell sample used herein preferably comprises cells of the ventral midbrain region or cultured cells containing in vitro differentiated dopaminergic neurons. In vitro differentiation of dopaminergic neurons can be carried out by known methods using cells, such as known ES cells, bone marrow interstitial cells, immortalized neuron-derived cell lines (Published Japanese Translation of International Publication No. Hei 8-509215; Published Japanese Translation of International Publication No. Hei 11-506930; Published Japanese Translation of International Publication No. 2002-522070), or primordial neuron cells (Published Japanese Translation of International Publication No. Hei 11-509729), as the starting material. Normally, dopaminergic neurons can be differentiated by co-culturing a tissue obtained from a dopaminergic neuron region of the brain, with a sustentacular cell layer derived from neural tissues. Moreover, methods are also known for deriving dopaminergic cells from neural tissues that normally do not produce dopamine, such as the striatum and cortex (Published Japanese Translation of International Publication No. Hei 10-509319). In addition, culturing under hypoxic conditions has been reported to produce cells containing a greater number of dopaminergic neurons (Published Japanese Translation of International Publication No. 2002-530068). A cell sample used in the selection of dopaminergic neuron progenitor cells of the present invention may be a cell population isolated or cultured by any method including the above-described methods.

In addition, it is necessary that a support used in immobilizing an antibody or a polypeptide of the present invention be safe to cells. Examples of such supports include synthetic or naturally-occurring organic polymer compounds, inorganic materials such as glass beads, silica gel, alumina, and activated charcoal, and those that have their surfaces coated with a polysaccharide or synthetic polymer. There are no particular limitations on the form of the support, examples of which include films, fibers, granules, hollow fibers, non-woven fabric, porous supports, or honeycombed supports, and the contact surface area can be controlled by changing its thickness, surface area, width, length, shape, and size in various ways.

<Dopaminergic Neuron Progenitor Cells>

Since cells acquired by using the expression of Lrp4 as an index are dopaminergic neuron proliferative progenitor cells prior to cell cycle exit, they are preferable in transplantation therapy for neurodegenerative diseases, such as Parkinson's disease, in terms of their safety, survival rate, and network formation ability, as compared to conventional mixed cell populations or dopaminergic neurons carrying an exogenous gene. Cells acquired by using expression of Lrp4 as an index can be used in transplanting directly or after growing in vitro (FIG. 6). Since dopaminergic neuron progenitor cells of the present invention that have been selected by using expression of Lrp4 as an index are proliferative progenitor cells, they are able to differentiate and mature at optimal locations in the brain, and can further proliferate in vivo, thereby resulting in expectations of long-term therapeutic effects. Moreover, since cells (populations) of the present invention obtained according to the method of the present invention are progenitor cells prior to cell cycle exit, they can also be differentiated into a suitable stage by selecting in vitro conditions, such as media, and are preferred materials for various types of neural transplantation therapy. For example, cells having a higher degree of safety in terms of transplanting can be obtained from the cells selected by using expression of Lrp4 as an index as described above, by additionally selecting using a postmitotic marker (for example, 65B13) as an index.

When neuron progenitor cells obtained using the methods of the present invention are used in transplants, preferably $1\times10^3$ to $1\times10^6$ neurons, and more preferably $5\times10^4$ to $6\times10^4$ neurons, are transplanted. The primary method is stereotaxic surgery in which a cell suspension is transplanted into the brain. In addition, cells may also be transplanted by microsurgery. See, Backlund et al. (Backlund et al. (1985) J. Neurosurg. 62: 169-73), Lindvall et al. (Lindvall et al. (1987) Ann. Neurol. 22: 457-68), or Madrazo et al. (Madrazo et al. (1987) New Engl. J. Med. 316: 831-4), for methods of transplanting neuron tissues.

Moreover, the cells of the present invention can also be used to isolate genes specific to dopaminergic neuron progenitor cells, and genes specific to each stage of the maturation from progenitor cells into dopaminergic neurons. They can also be used to search for therapeutic targets for Parkinson's disease, elucidate the maturation process of dopaminergic neurons, and in screenings using maturation as an indicator.

<Comparison of Gene Expression Levels>

Dopaminergic neuron progenitor cells, which were obtained using an antibody of the present invention, can be used as a material to isolate genes specifically expressed in these cells. They can also be used to investigate and isolate genes specifically expressed in cells that have differentiated, induced, or proliferated from the dopaminergic neuron progenitor cells of the present invention. In addition, they can also be used to investigate genes required for in vivo differentiation of dopaminergic neurons, by investigating genes that have different expression levels between cells that have differentiated, induced, or proliferated and the original progenitor cells. Since such genes are potential candidates for treating diseases caused by defects in dopaminergic neurons, their determination and isolation are extremely useful.

Comparison of gene expression levels in dopaminergic neuron progenitor cells of the present invention with those of cells that have differentiated, induced, or proliferated therefrom, or other cells; or comparison of gene expression levels of the differentiated, induced, or proliferated cells with those of other cells, can be done by commonly used methods, such as cell in situ hybridization, Northern blot hybridization, RNA dot blot hybridization, reverse transcription PCR, RNase protection assay, DNA microarray hybridization, serial analysis of gene expression (SAGE) (Velculescu et al. (1995) Science 270: 484-487), subtractive hybridization, and representation difference analysis (RDA) (Lisitsyn (1995) Trends Genet. 11: 303-307).

For cellular in situ hybridization, locations where RNA processing, transport, and localization into the cytoplasm occur in individual cells can be investigated, by hybridizing total RNA or poly A$^+$ RNA prepared from cells with a labeling probe specific to a given RNA sequence. In addition, RNA size can be determined by size fraction using gel electrophoresis. Moreover, RNA transcription products can be visualized in situ by using quantitative fluorescent in situ hybridization (FISH) and a digital imaging microscope (Femino et al. (1998) Science 280: 585-90), which are applicable to the present invention.

When using reverse transcription PCR for gene expression analysis, the expression of a specific gene can be roughly quantified. Various isoforms of a single RNA transcription product can also be detected and analyzed using the present method. For reverse transcription PCR, when the reaction is carried out using exon-specific primers, and amplification products other than the predicted product are detected, mRNA isoforms produced by alternative splicing can be identified by analyzing these products. See, for example, the method described in Pykett et al. (1994) Hum. Mol. Genet. 3: 559-64, for details. When a quick and rough analysis of expression pattern is demanded, the present method which uses the PCR of the present invention is particularly preferred, in terms of its high speed, high sensitivity, and simplicity.

The efficiency of gene expression screening can be improved by using a DNA chip. Here, a DNA chip refers to a miniature array, in which oligonucleotides, DNA clones, or such, are immobilized at a high density on a support surface, such as glass. For example, in order to carry out multiple expression screening, cDNA clones for each gene of interest, or oligonucleotides specific to each gene, are immobilized on a chip to produce a microarray. Next, RNAs are prepared from dopaminergic neuron proliferative progenitor cells of the present invention, or cells differentiated, induced, or proliferated therefrom, and treated with reverse transcriptase to yield cDNAs. Next, the resulting cDNA sample is labeled with fluorescent tags or other tags, and then hybridized to the microarray. As a result, genes that are actively expressed in the cells have a higher percentage of the total labeled cDNA, while genes that are not significantly expressed have a lower percentage. Namely, the fluorescent signal intensity which represents hybridization between a labeled cDNA and a cDNA clone or an oligonucleotide on the chip, reflects the expression level of each sequence in the labeled cDNA, and thereby enables the quantification of gene expression.

In addition, multiple genes in dopaminergic neuron progenitor cells of the present invention, or cells differentiated, induced, or proliferated therefrom, can be simultaneously analyzed by mRNA differential display, which involves reverse transcription PCR using degenerate PCR primers. First, a modified oligo dT primer is prepared, in which one or two nucleotides at the 3' terminus in the poly A tail of a given mRNA have been altered. Then, a reverse transcription reaction is carried out using the total RNAs isolated from the progenitor cells of the present invention, cells differentiated or proliferated therefrom, or control cells to be used for expression comparison (Liang et al. (1993) Nucleic Acids Res. 21: 3269-3275). If the altered nucleotide is a "G", then mRNA having a "C" immediately before the poly A tail can be selectively amplified. If the altered nucleotides are "CA", then mRNA having "TG" immediately before the poly A tail can be selectively amplified. Next, an arbitrary nucleotide sequence of about 10 nucleotides in length is prepared for use as a second primer, and a PCR amplification reaction is carried out using the modified oligo dT primer and this second primer. The amplification product is subjected to size fractionation by electrophoresis using a long polyacrylamide gel. By using such a method, cDNA derived from mRNA specifically expressed in either the cells of the present invention or the control cells can be detected as a band only present in the either sample that has been electrophoresed. This method can also be used to analyze expression of unidentified genes.

SAGE analysis does not require a special device for detection, and is one of the preferred analytical methods for simultaneously detecting the expression of a large number of transcription products. First, poly A+ RNA is extracted from the dopaminergic neuron progenitor cells of the present invention, or cells differentiated, induced, or proliferated therefrom, using standard methods. Next, the RNA is converted into cDNA using a biotinylated oligo (dT) primer, and then treated with a four-base recognizing restriction enzyme (Anchoring Enzyme: AE). Here, the AE-treated fragments contain a biotin group at their 3' terminus. Next, the AE-treated fragments are incubated with streptoavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the IIS-type restriction enzyme (cleaves at a predetermined location no more than 20 bp away from the recognition site) serving as a tagging enzyme (TE), and (3) an additional sequence of sufficient length for constructing a PCR-specific primer. Herein, the linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a read-out of consecutive ditags of constant length. The presence of mRNA corresponding to each tag can then be identified once from the determination of the clone's nucleotide sequence and information on the sequence tags thus obtained.

Subtraction hybridization is frequently used for cloning a gene with different expression levels in various tissues or cells, and can also be used to clone a gene specifically expressed in dopaminergic neuron progenitor cells of the present invention, or cells differentiated, induced, or proliferated therefrom. First, from the aforementioned cells of the present invention, a DNA sample of cells to be tested is prepared (hereinafter referred to as "test DNA"). Next, DNA of cells to be compared is prepared (hereinafter referred to as "driver DNA"). The test DNA and the driver DNA can also be used interchangeably. In any case, genes present in the test DNA but not present in the driver DNA are detected. Next, the prepared test DNA is mixed with a large excess of driver DNA, and denatured to form single-stranded DNA, followed by annealing. A specific sequence not present in the driver DNA can be isolated as double-stranded DNA comprising only the test DNA sequence by regulating the annealing conditions. See, Swaroop et al. (1991) Nucleic Acids Res. 19: 1954 and Yasunaga et al. (1999) Nature Genet. 21: 363-9, for further details on this method.

The RDA method is a method that uses PCR to selectively amplify a sequence of the test DNA that is not present in the driver DNA, and can be similarly used in the present invention like the other previously described methods. See, Lisitsyn (1995) Trends Genet. 11: 303-7 and Schutte et al. (1995) Proc. Natl. Acad. Sci. USA 92: 5950-4, for more details on the procedure.

Genes specific to dopaminergic neuron progenitor cells, or cells differentiated, induced, or proliferated therefrom, are detected and isolated as described, and can be inserted into vectors or such, for sequence determination and expression analysis using the various known methods described above.

<Screening Using Progenitor Cell Maturation as an Index>

The present invention provides a screening method that comprises a step of contacting a test substance with dopaminergic neuron progenitor cells of the present invention, and a step of detecting differentiation or proliferation of the progenitor cells resulting from that contact. Since compounds obtained by this screening method demonstrate a regulatory function in the differentiation, proliferation, and such, of dopaminergic neurons, they are considered useful as potential therapeutic candidates for diseases caused by defects in dopaminergic neurons.

Here, the "test substance" may be any type of compound, examples of which include the expression products of gene libraries, synthetic low molecular weight compound libraries, synthetic peptide libraries, antibodies, substances released by bacteria, cell (microbial, plant, or animal) extracts, cell (microbial, plant, or animal) culture supernatants, purified or partially purified polypeptides, marine organisms, plant or animal extracts, soil, random phage peptide display libraries, and such.

Cell differentiation and proliferation can be detected by comparing with the status of the cell in the absence of the test substance. Cell differentiation and proliferation may be detected by morphological observation under a microscope or by detection and quantification of substances produced in cells, such as dopamine.

<Analysis of Lrp4 Expression Regulatory Region>

An expression regulatory region of Lrp4 can be cloned from genomic DNA by known methods using a sequence of the Lrp4 gene. For example, a method for establishing the transcriptional start site, such as the S1 mapping method, is known and can be used (Cell Engineering, Supplement 8, New Cell Engineering Experiment Protocol, Cancer Research Division, The Institute of Medical Science, The University of Tokyo ed., Shujunsha Publishing (1993) pp. 362-374). In general, the expression regulatory region of a gene can be cloned by screening a genomic DNA library, using a probe DNA comprising a 15-100 bp segment, and preferably a 30-50 bp segment, of the gene's 5' terminus (in the present invention, all or a portion of nucleotides of SEQ ID NO: 1 or SEQ ID NO: 2). A clone obtained in this manner contains a 5' non-coding region of 10 kbp or more, and is shortened or fragmented by exonuclease treatment, or such. Finally, the shortened sequence portion, comprising a potential expression regulatory region, is evaluated for strength, regulation, and such, of its expression using a reporter gene, thereby making it possible to determine the minimum unit required for maintaining the activity of the Lrp4 expression regulatory region.

Gene expression regulatory regions can be predicted using a program such as Neural Network (on with world wide web at fruitfly.org./seq_tools/promoter.html; Reese et al., Biocomputing: Proceedings of the 1996 Pacific Symposium, Hunter and Klein ed., World Scientific Publishing Co., Singapore, (1996)). Moreover, a program for predicting the minimum unit required for the activity of an expression regulatory region is also known, (on the world wide web at biosci.cbs.umn.edu./software/proscan/promoterscan.htm; Prestridge (1995) J. Mol. Biol. 249: 923-932), and can be used.

The expression regulatory region of the Lrp4 gene isolated in this manner can be used to produce a protein of interest specifically in dopaminergic neuron proliferative progenitor cells prior to cell cycle exit in vivo.

<Ligand for Lrp4>

The Lrp4 polypeptides have a transmembrane domain, and thus are thought to exist embedded within the cell membrane in nature. Due of its expression in dopaminergic neuron proliferative progenitor cells before cell cycle exit, Lrp4 is believed to be involved in the regulation of progenitor cell proliferation and in neuron differentiation and maturation. Thus, potential ligands that may demonstrate an agonistic or antagonistic function towards Lrp4 may be used for regulating the differentiation of dopaminergic neurons in vivo, ex vivo, and in vitro. In identifying a ligand for an Lrp4 polypeptide, the Lrp4 polypeptide and a candidate compound are first contacted and tested for the presence of binding. In this case, the Lrp4 polypeptide can be used when immobilized on a support, or embedded in the cell membrane. There are no particular limitations on the candidate compounds, examples of which include expression products of gene libraries, natural substances derived from marine organisms, extracts of various types of cells, known compounds and peptides, natural substances derived from plants, body tissue extracts, microbial culture supernatants and peptide groups randomly produced by the phage display method (J. Mol. Biol. 222: 301-10 (1991)). In addition, the candidate compound may be labeled for detection of binding.

<Inhibition of Lrp4 Expression>

Since it is clearly demonstrated by the present invention that Lrp4 is transiently expressed in dopaminergic neuron proliferative progenitor cells prior to cell cycle exit, Lrp4 may be involved in the control of the proliferation of progenitor cells as well as neuron differentiation and maturation. Thus, substances that inhibit the expression of the Lrp4 gene may be used to control the differentiation of dopaminergic neurons in vivo, ex vivo, and in vitro. Examples of substances capable of inhibiting gene expression include antisense nucleic acids, ribozymes, and double-stranded RNA (small interfering RNA; siRNA). Thus, the present invention provides such antisense nucleic acids, ribozymes, and double-stranded RNA.

Examples of antisense mechanisms that suppress target gene expression include: (1) inhibition of transcription initiation via triplex formation, (2) transcription suppression through hybrid formation at sites of local open-loop structures formed by RNA polymerase, (3) transcription inhibition through hybrid formation with RNA during synthesis, (4) suppression of splicing through hybrid formation at intron-exon junctions, (5) suppression of splicing through hybrid formation at sites of spliceosome formation, (6) suppression of mRNA migration to the cytoplasm through hybrid formation with mRNA, (7) suppression of splicing through hybrid formation at a capping site or poly A addition site, (8) suppression of translation initiation through hybrid formation at binding sites of translation initiation factors, (9) translation suppression through hybrid formation at ribosome binding sites, (10) suppression of peptide chain elongation through hybrid formation at mRNA coding regions or polysome binding sites, and (11) suppression of gene expression through hybrid formation at sites of nucleic acid/protein interaction (Hirashima and Inoue, "New Biochemistry Experiment Course 2, Nucleic Acids IV, Gene Replication and Expression", Japanese Biochemical Society edit., Tokyo Kagaku Dozin Publishing, pp. 319-347 (1993)).

An Lrp4 antisense nucleic acid of the present invention may be a nucleic acid that inhibits gene expression by any of the mechanisms described in (1) to (11) above. Namely, it may contain an antisense sequence to not only a sequence of a coding region, but also a sequence of a non-coding region of a target gene whose expression is to be inhibited. A DNA that encodes an antisense nucleic acid can be used by linking to a suitable regulatory sequence that allows its expression. The antisense nucleic acid does not need to be completely complementary to the coding region or non-coding region of a target gene, as long as it can effectively inhibit the expression of this gene. Such antisense nucleic acids have a chain length of at least 15 bp or more, preferably 100 bp or more, and more preferably 500 bp or more, and are normally within 3000 bp, preferably within 2000 bp, and more preferably within 1000 bp. It is preferable that such antisense nucleic acids share an identity of 90% or more, and more preferably 95% or more, with the complementary chain of a target gene transcription product. These antisense nucleic acids can be prepared according to the phosphorothionate method (Stein (1988) Nucleic Acids Res. 16: 3209-21) or the like, using an Lrp4 polynucleotide.

"Ribozyme" is a generic term referring to catalysts with an RNA component, and ribozymes are broadly classified into large ribozymes and small ribozymes. Large ribozymes cleave the phosphate-ester bonds of a nucleic acid, and after reaction, they leave 5'-phosphoric acid and 3'-hydroxyl group at the reaction sites. Large ribozymes are further classified into (1) group I intron RNAs, which carry out guanosine-initiated trans-esterification reactions at 5'-splice sites, (2) group II intron RNAs, which perform two-step self-splicing reactions via a lariat structure, and (3) RNA components of ribonuclease P, which cleave precursor tRNAs at their 5' side via hydrolysis reactions. In contrast, small ribozymes are comparatively small structural units (about 40 bp) that cleave RNAs, forming 5'-hydroxyl groups and 2'-3' cyclic phosphoric acids. Small ribozymes include, for example, hammerhead-type ribozymes (Koizumi et al. (1988) FEBS Lett. 228: 225) and hairpin-type ribozymes (Buzayan (1986) Nature 323: 349; Kikuchi and Sasaki (1992) Nucleic Acids Res. 19: 6751; Kikuchi (1992) Chemistry and Biology 30: 112). Since ribozymes are easily altered and synthesized, various modification methods are known. For example, hammerhead-type ribozymes that recognize and cleave nucleotide sequence UC, UU, or UA within a target RNA can be created, by designing the substrate binding portion of a ribozyme to be complementary to an RNA sequence near the target site (Koizumi et al. (1988) FEBS Lett. 228: 225; M. Koizumi and E. Ohtsuka (1990) Protein, Nucleic Acid and Enzyme 35: 2191; Koizumi et al. (1989) Nucleic Acids Res. 17: 7059). Hairpin-type ribozymes can also be designed and produced using known methods (Kikuchi and Sasaki (1992) Nucleic Acids Res. 19: 6751; Kikuchi (1992) Chemistry and Biology 30: 112).

Antisense nucleic acids and ribozymes of the present invention can also be used in virus vectors derived from retroviruses, adenoviruses, adeno-associated viruses, and such, or non-virus vectors that use liposomes, or naked DNAs, to control gene expression in cells using ex vivo or in vivo gene therapy.

In 1998, a phenomenon was observed in nematodes in which RNAs interfere with each other causing them to lose function (RNA interference) (Fire et al. (1998) Nature 391: 806-11). RNA interference is a phenomenon in which, when an artificial double-stranded RNA is introduced into cells, RNAs having the same nucleotide sequence are degraded. As a result of subsequent research, it is suggested that RNA silencing phenomena such as RNA interference are cellular mechanisms for eliminating defective mRNA and defending the cells against transposons, viruses, and other parasites. At present, double-stranded RNAs (small interfering RNAs; siRNAs) are used as tools for suppressing the expression of numerous genes, and methods of treating and preventing diseases are being studied to suppress the expression of genes that cause diseases through the use of siRNA. There are no particular limitations on an siRNA of the present invention, provided it inhibits transcription of Lrp4 mRNA. Normally, the siRNA is a combination of a sense chain and antisense chain to the sequence of a target mRNA, and has a nucleotide length of from at least 10 to the same number of nucleotides as the target mRNA. This siRNA preferably has a nucleotide length of 15 to 75, preferably 18 to 50, and more preferably 20 to 25 nucleotides.

In order to suppress Lrp4 expression, siRNA can be introduced into a cell using known methods. For example, a DNA encoding in a single strand two RNA chains that compose an siRNA is designed and then incorporated into an expression vector, cells are transformed with the expression vector, and the siRNA can be expressed in the cells in the form of double-stranded RNA having a hairpin structure. Plasmid expression vectors that continuously produce siRNA by transfection have also been designed (for example, RNAi-Ready pSIREN Vector™, and RNAi-Ready pSIREN-RetroQ Vector™ (BD Biosciences Clontech)).

The nucleotide sequence of an siRNA can be designed using a computer program such as that disclosed at the Ambion website (on the world wide web at ambion.com/techlib/misc/siRNA_finder.html). Kits for screening for functional siRNAs are also commercially available and can be used (for example, BD Knockout RNAi System™ (BD Biosciences Clontech).

BEST MODE FOR CARRYING OUT THE INVENTION

The present invention will be explained in more detail with reference to examples, but should not be construed as being limited thereto.

Figure 1:
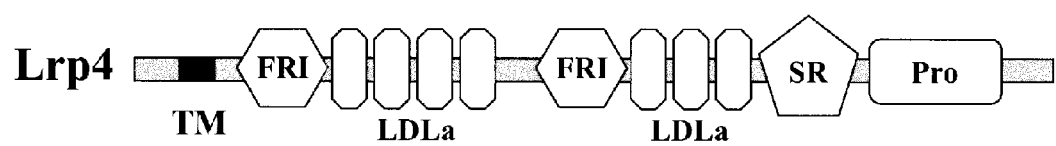
FIG. 1 schematically shows the structure of Lrp4. TM: transmembrane domain, FRI: frizzeled domain, LDLa: LDL receptor domain, SR: scavenger receptor domain, Pro: serine protease domain.

1. Isolation and Sequence Analysis of a Gene Specific to Dopaminergic Neuron Progenitor Cells To isolate a gene specific to dopaminergic neuron progenitor cells, the midbrain ventral region of E12.5 mice was additionally cut into two regions in the dorsoventral direction, and genes specifically expressed in the most ventral region containing dopaminergic neurons were identified by the subtraction (N-RDA) method. One of the isolated cDNA fragments was a fragment encoding Lrp4/Corin. Lrp4 encodes type II transmembrane proteins (FIG. 1).

(1) N-RDA Method
(1)-1. Adapter Preparation

The following oligonucleotides were annealed to each other, and prepared at 100 µM.

(ad2: ad2S + ad2A, ad3: ad3S + ad3A, ad4: ad4S + ad4A, ad5: ad5S + ad5A, ad13: ad13S + ad13A)

| | | |
|---|---|---|
| ad2S: | cagctccacaacctacatcattccgt | (SEQ ID NO: 5) |
| ad2A: | acggaatgatgt | (SEQ ID NO: 6) |
| ad3S: | gtccatcttctctctgagactctggt | (SEQ ID NO: 7) |
| ad3A: | accagagtctca | (SEQ ID NO: 8) |
| ad4S: | ctgatgggtgtcttctgtgagtgtgt | (SEQ ID NO: 9) |
| ad4A: | acacactcacag | (SEQ ID NO: 10) |
| ad5S: | ccagcatcgagaatcagtgtgacagt | (SEQ ID NO: 11) |
| ad5A: | actgtcacactg | (SEQ ID NO: 12) |
| ad13S: | gtcgatgaacttcgactgtcgatcgt | (SEQ ID NO: 13) |
| ad13A: | acgatcgacagt. | (SEQ ID NO: 14) |

(1)-2. cDNA Synthesis

Ventral midbrain regions were cut out of E12.5 mouse embryos (Japan SLC), and divided into two sections in the dorsoventral direction, Total RNA was prepared using the RNeasy Mini Kit™ (Qiagen), and double-stranded cDNA was synthesized using a cDNA Synthesis Kit™ (Takara). After digestion with restriction enzyme RsaI, ad2 was added. The cDNA was amplified by a 5-minute incubation at 72° C., 15 PCR cycles of 30 seconds at 94° C., 30 seconds at 65° C., and 2 minutes at 72° C., and a final 2-minute incubation at 72° C. using ad2S as the primer. In all cases, N-RDA PCR was carried out using a reaction solution containing the following components.

10× ExTaq 5 µl
2.5 mM dNTP 4 µl
ExTaq 0.25 µl
100 µM primer 0.5 µl
cDNA 2 µl
Distilled water 38.25 µl (1)-3. Driver Production The ad2S amplified cDNA was further amplified by incubating at 94° C. for 2 minutes, and then performing five PCR cycles of 30 seconds at 94° C., 30 seconds at 65° C., and 2 minutes at 72° C., and a final 2-minute incubation at 72° C. The cDNA was purified using the Qiaquick PCR Purification Kit™ (Qiagen), and digested with RsaI. 3 µg was used for each round of subtraction, (1)-4. Tester Production The ad2S amplified cDNA was further amplified by incubating at 94° C. for 2 minutes, and then performing five PCR cycles of 30 seconds at 94° C., 30 seconds at 65° C., and 2 minutes at 72° C., and a final 2-minute incubation at 72° C. The cDNA was purified using the Qiaquick PCR Purification Kit™ (Qiagen), and digested with RsaI. ad3 was added to 60 ng of the RsaI-digested cDNA.

(1)-5. First Round of Subtraction

The tester and the driver produced in Sections 1-3 and 1-4 above were mixed, ethanol precipitated, and then dissolved in 1 µl of 1×PCR buffer. After a 5-minute incubation at 98° C., 1 µl of 1×PCR buffer+1M NaCl was added. After another 5 minutes of incubation at 98° C., the tester and the driver were hybridized at 68° C. for 16 hours.

With ad3S as the primer, the hybridized cDNA was amplified by incubating at 72° C. for 5 minutes, and performing 10 cycles of 30 seconds at 94° C., 30 seconds at 65° C., and 2 minutes at 72° C. Next, the amplified cDNA was digested with the Mung Bean Nuclease (Takara) and purified using the Qiaquick PCR Purification Kit™. Then, it was amplified by incubating at 94° C. for 2 minutes, and performing 13 PCR cycles of 30 seconds at 94° C., 30 seconds at 65° C., and 2 minutes at 72° C., and a final 2-minute incubation at 72° C.

(1)-6. Normalization

1 µl of 2×PCR buffer was added to 8 ng of the cDNA amplified in the first round of subtraction. After incubating at 98° C. for 5 minutes, 2 µl of 1×PCR buffer+1M NaCl was added. After another 5 minutes of incubation at 98° C., the cDNA was hybridized at 68° C. for 16 hours.

The hybridized cDNA was digested with RsaI, and purified using the Qiaquick PCR Purification Kit™. Then, it was amplified with ad3S as the primer by incubating at 94° C. for 2 minutes, and performing 11 PCR cycles of 30 seconds at 94° C., 30 seconds at 65° C., and 2 minutes at 72° C., and a final 2-minute incubation at 72° C. The PCR product was then digested with RsaI, followed by the addition of ad4.

(1)-7. Second Round of Subtraction 20 ng of cDNA to which ad4 was added in Section 1-6 above was used as the tester and mixed with the driver of 1-3 above, and the same subtraction procedure used in Section 1-5 above was performed. Finally, ad5 was added to the cDNA following RsaI digestion.

(1)-8. Third Round of Subtraction 2 ng of cDNA to which ad5 was added in section 1-7 above was used as the tester and mixed with the driver of 1-3 above, and the same subtraction procedure used in section 1-5 above was carried out. Finally, ad13 was added to the RsaI-digested cDNA.

(1)-9. Fourth Round of Subtraction 2 ng of cDNA to which ad13 was added in section 1-8 above was used as the tester and mixed with the driver of 1-3 above, and the same subtraction procedure used in Section 1-5 above was carried out. The amplified cDNA was cloned into pCRII™ vector (Invitrogen), and its nucleotide sequence was analyzed using the ABI3100 sequence analyzer.

2. Expression Analysis of the Lrp4 Gene

Next, an expression analysis of the Lrp4 gene by in situ hybridization was carried out according to the following protocol.

First, E12.5 mouse embryos were embedded in O.C.T., and fresh frozen sections of 16 µm thickness were prepared. After drying on a slide glass, the sections were fixed in 4% PFA at room temperature for 30 minutes. After washing with PBS, hybridization was carried out at 65° C. for 40 hours (1 µg/ml DIG-labeled RNA probe, 50% formamide, 5×SSC, 1% SDS, 50 µg/ml yeast RNA, 50 µg/ml Heparin). Subsequently, the sections were washed at 65° C. (50% formamide, 5×SSC, 1% SDS) and then treated with RNase (5 µg/ml RNase) at room temperature for 5 minutes. After washing with 0.2×SSC at 65° C. and washing with 1×TBST at room temperature, blocking was carried out (Blocking reagent: Roche). The sections were then reacted with alkaline phosphatase-labeled anti-DIG antibody (DAKO), washed (1×TBST, 2 mM Levamisole), and color developed using NBT/BCIP (DAKO) as the substrate.

Figure 2:
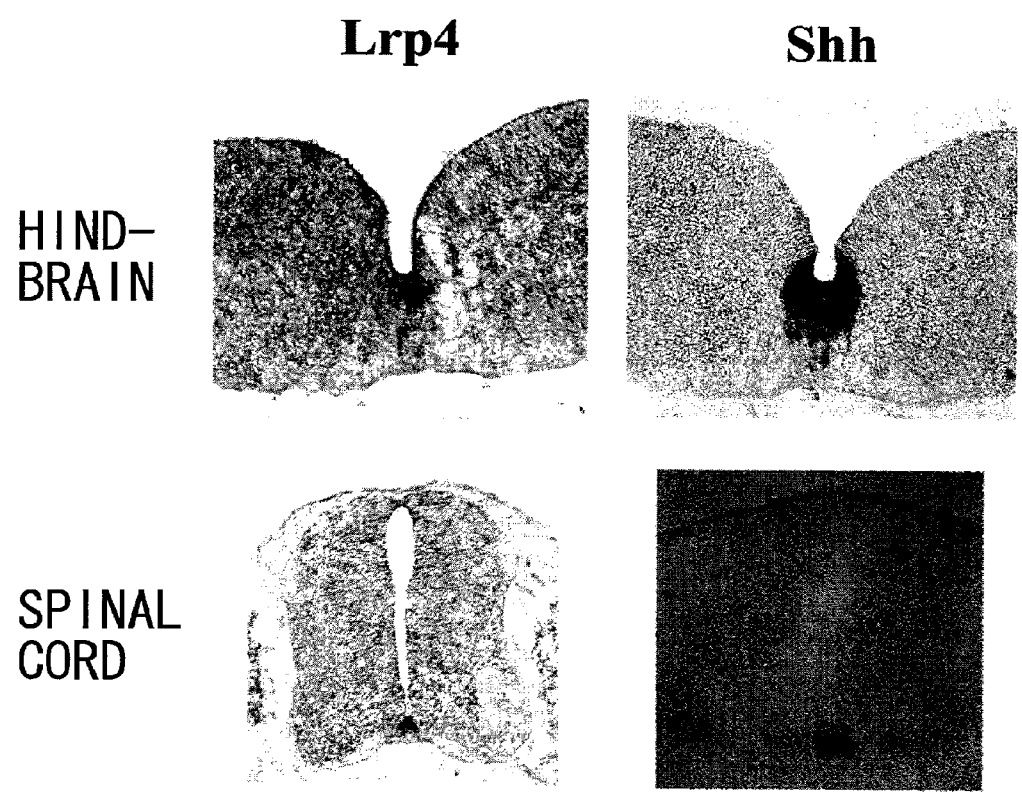
FIG. 2 is a set of photographs showing the results of Lrp4 and Shh mRNA expression analysis in E12.5 mouse hindbrain ventral region and spihal cord by in situ hybridization.
Figure 3:
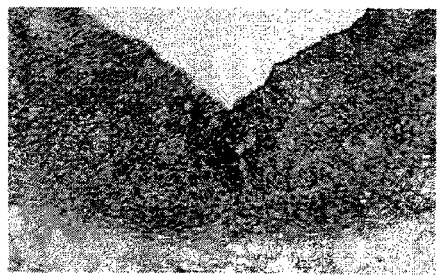
FIG. 3 is a set of photographs showing the results of Lrp4, Shh, tyrosine hydroxylase (TH), and NCAM mRNA expression analysis in E12.5 mouse midbrain ventral region by in situ hybridization.
Figure 3:
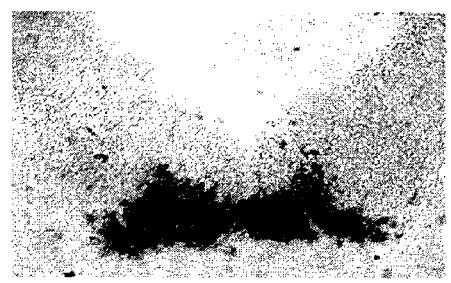
Figure 3:
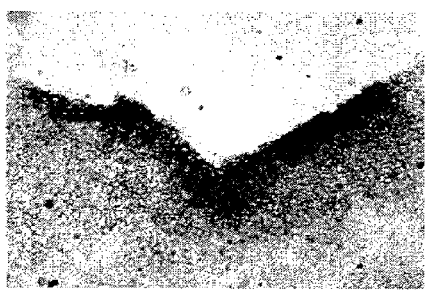
Figure 3:
Figure 7:
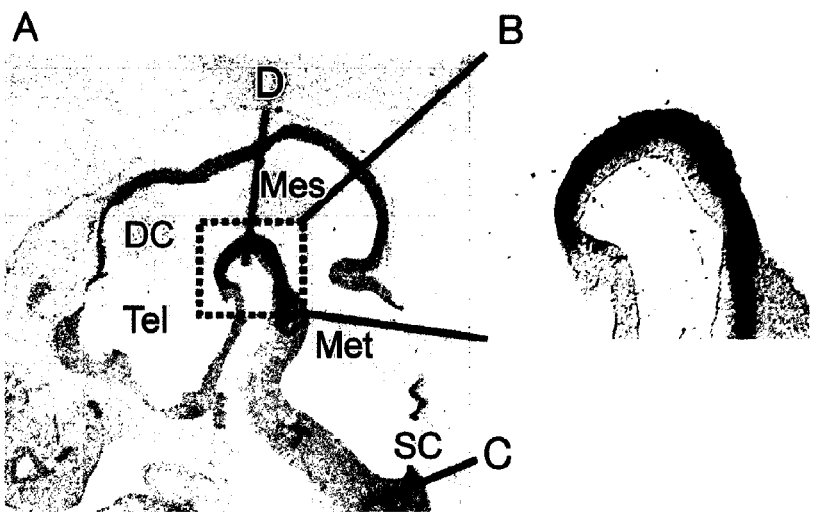
FIG. 7A-D are a set of photographs showing the results of Lrp4 mRNA expression analysis in E12.5 mouse central nervous system by in situ hybridization. A: sagittal cross-section, B: enlarged photograph of the area inside the box of A, C: cross-section at the location of the red line of A, D: Expression of Lrp4, Shh, and tyrosine hydroxylase (TH) mRNA in E12.5 mouse midbrain ventral region.
Figure 7:
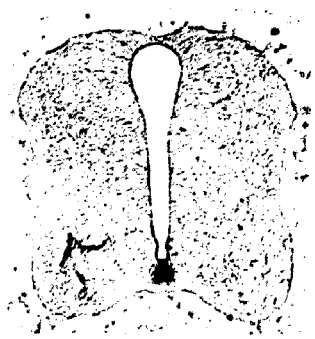
Figure 7:
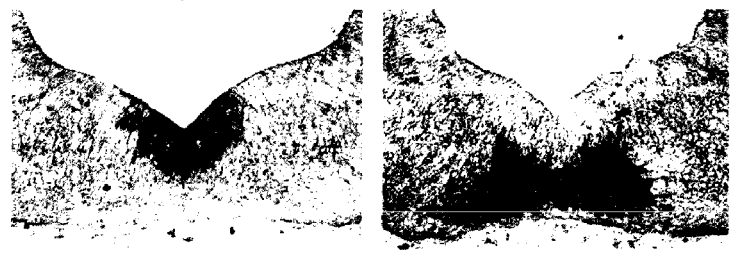
Figure 7:
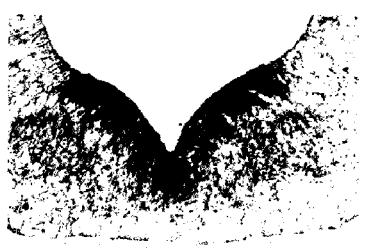

The expression analysis by in situ hybridization showed that Lrp4 is specifically expressed in the ventral midline region from the midbrain to the hindbrain and the spinal cord at the stage E12.5, which corresponds to the time of dopaminergic neuron development. Lrp4 demonstrates a similar expression pattern to Shh from the hindbrain to the spinal cord, and was clearly determined to be specific to the floor plate, the organizer region (FIGS. 2 and 7). In the midbrain, Lrp4 expression was observed more centrally than the Shh expression zone (FIGS. 3 and 7).

Figure 4:
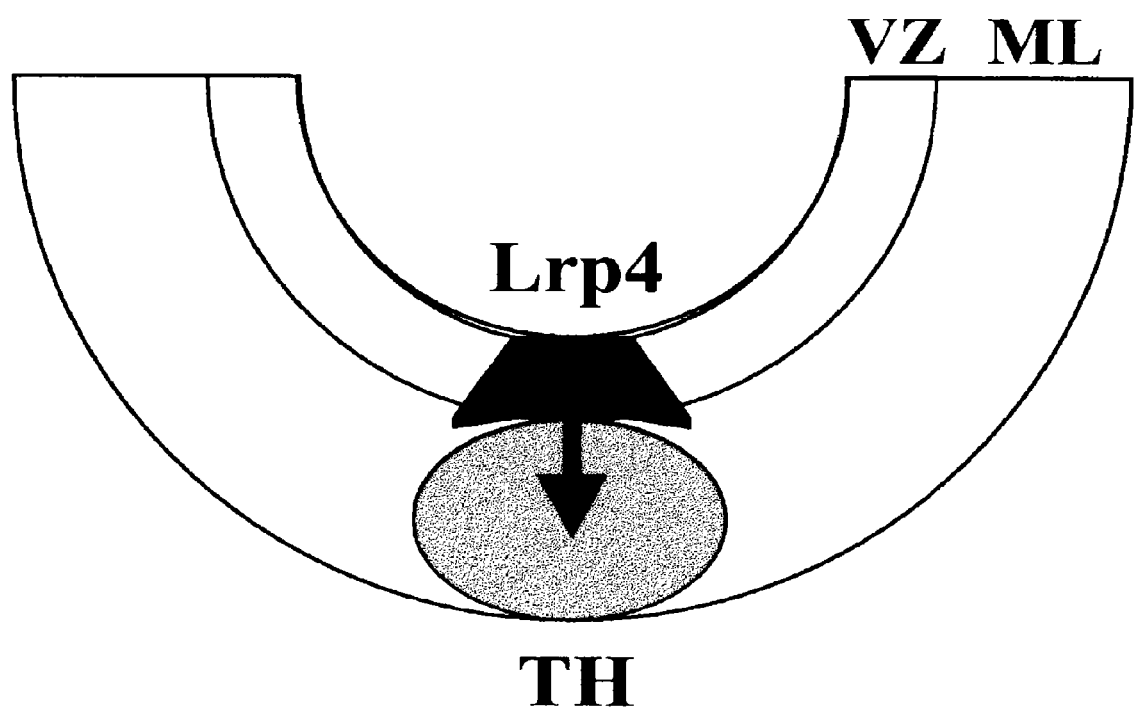
FIG. 4 schematically shows the expression pattern of Lrp4 in the midbrain. VZ: ventricular zone, ML: mantle layer.
Figure 5:
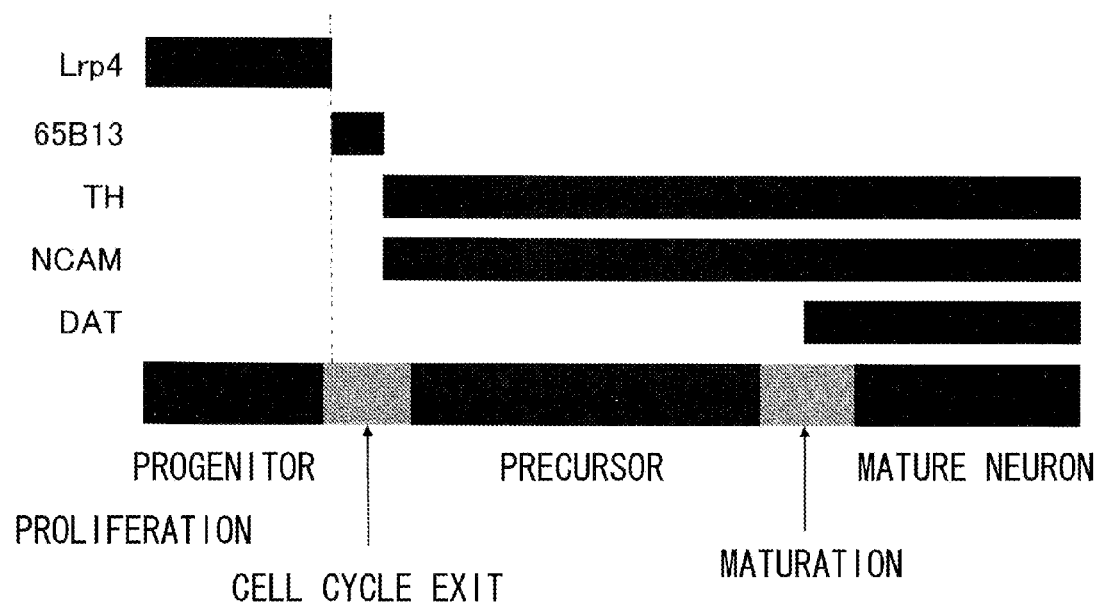
FIG. 5 schematically shows the expression timings of Lrp4, 65B13, TH, NCAM, and DAT from generation to maturation of dopaminergic neurons.
Figure 6:
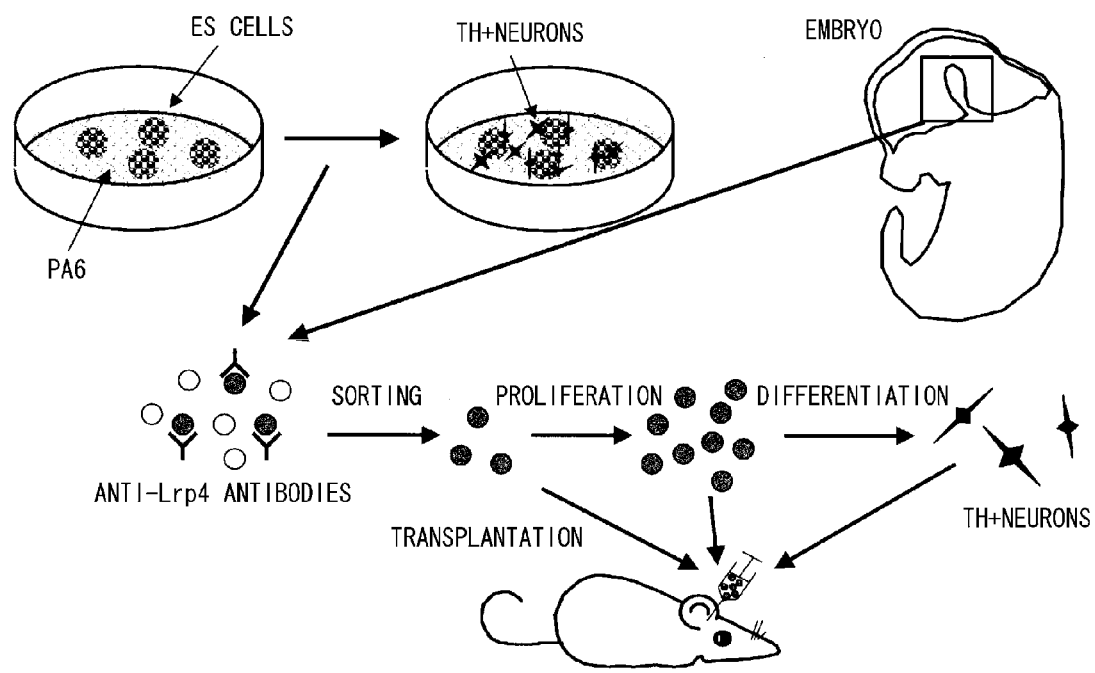
FIG. 6 schematically shows the isolation methods of dopaminergic neuron proliferative progenitor cells using anti-Lrp4 antibodies and its utilization.

As a result of comparing with NCAM, a neuron maturation marker, Lrp4-expressing cells were proliferative progenitor cells in the NCAM-negative ventricular zone (VZ). Moreover, when compared with the expression of the dopamine neuron marker, tyrosine hydroxylase (TH), although expression of both TH and Lrp4 in the same cells was not observed since TH is only expressed in the mantle layer (ML), their expression regions completely overlapped along the dorsal-ventral axis (FIGS. 3 and 7). In general, neurons present in neural tubes are known to first proliferate in the VZ, exit cell cycle with the commencement of differentiation, and then mature after migrating to the outer ML. Thus, progenitor cells of dopaminergic neurons are believed to proliferate in the VZ which lines the TH expression zone, and express TH after having migrated to the outside following the cell cycle exit. Namely, Lrp4 is believed to be specifically expressed in the midbrain in dopaminergic neuron progenitor cells (FIGS. 4 and 5).

3. Expression of Lrp4 in Dopaminergic Neurons Induced to Differentiate from ES Cells Next, whether Lrp4 is expressed in ES cells that have been induced to differentiate into dopaminergic neurons in vitro, was examined.

First, dopaminergic neurons were induced to differentiate from ES cells using the SDIA method (Kawasaki et al. (2000) Neuron 28(1): 31-40) (see the upper part of FIG. 8). Cells were recovered 4, 6, 8, 10, and 12 days after induction, and total RNA was recovered using the RNeasy Mini Kit™ (Qiagen) followed by RT-PCR. In RT-PCR, cDNA was initially synthesized for 1 µg of total RNA using the RNA PCR Kit™ (TaKaRa). PCR was then carried out in the following reaction system using as template cDNA equivalent to 10 ng, 1 ng, and 0.1 ng.

| | |
|---|---|
| 10× ExTaq | 2 µl |
| 2.5 mM dNTP | 1.6 µl |
| ExTaq | 0.1 µl |
| 100 µM primer | 0.2 µl each |
| cDNA | 1 µl |
| Distilled water | 14.9 µl |

After incubating for 2 minutes at 94° C., 35 PCR cycles of 30 seconds at 94° C., 30 seconds at 65° C., and 2 minutes at 72° C. were carried out followed by incubating for 2 minutes at 72° C.

The sequences of the primers used are shown below.

```
Lrp4 (SEQ ID NOS: 15 and 16):
TAGTCTACCACTGCTCGACTGTAACG/CAGAGTGAACCCAGTGGACA
TATCTG TH (SEQ ID NOS: 17 and 18):
GTTCCCAAGGAAAGTGTCAGAGTTGG/GAAGCTGGAAAGCCTCCAGG
TGTTCC DAT (SEQ ID NOS: 19 and 20):
CTCCGAGCAGACACCATGACCTTAGC/AGGAGTAGGGCTTGTCTCCC
AACCTG
```

Figure 8:
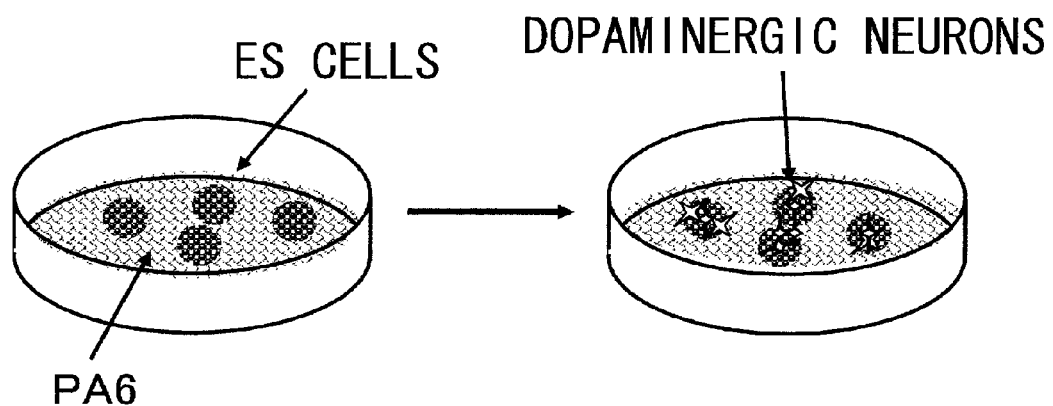
FIG. 8 shows the expression of Lrp4 from ES cells in an in vitro dopaminergic neuron differentiation system. The top of the drawing schematically shows the differentiation of dopaminergic neurons from ES cells. The bottom photograph shows the results of investigating the expression of Lrp4 in dopaminergic neurons differentiated from ES cells using the SDIA method by RT-PCR over time.
Figure 8:
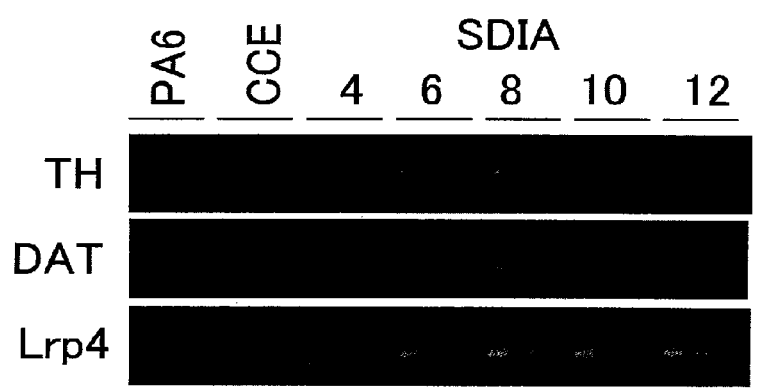

According to the results of expression analysis by RT-PCR, although Lrp4 is not expressed in ES cells (CCE) or stroma cells (PA6), expression was clearly induced starting on day 4 in the same manner as TH as a result of inducing differentiation (FIG. 8). Thus, Lrp4 is useful as a marker not only when isolating dopaminergic neuron proliferative progenitor cells from fetal midbrain, but also when isolating dopaminergic neuron proliferative progenitor cells that have been induced to differentiate from ES cells in vitro.

INDUSTRIAL APPLICABILITY

Lrp4, a gene expressed specifically and transiently in dopaminergic neuron proliferative progenitor cells before cell cycle exit, was identified according to the present invention. The cellular expression of Lrp4 can be used as an indicator in selecting suitable cells to be used in transplantation therapy for neurodegenerative diseases, such as Parkinson's disease, in terms of their safety, survival rate, and network formation ability. In addition, since neural proliferative progenitor cells before cell cycle exit are selectively obtained, they can be easily differentiated into an appropriate state in vitro when used in therapy that requires mature cells. Moreover, dopaminergic neuron proliferative progenitor cells obtained using the genes of the present invention can also be used to isolate genes specifically expressed in these cells. The cells are also thought to be useful in developing pharmaceuticals for neurodegenerative diseases such as Parkinson's disease. Since dopaminergic neuron proliferative progenitor cells before cell cycle exit are involved in early neuron formation, they are useful in elucidating the neuron maturation process, namely, identifying various factors involved in the maturation process. Elucidation of these factors is expected to contribute greatly to the treatment of neurodegenerative diseases. Moreover, maturation of these cells can be used as an index for screening substances that may regulate (inhibit or promote) the maturation process.

The invention claimed is:

1. A method of selecting a dopaminergic neuron proliferative progenitor cell, wherein the method comprises the step of contacting a polynucleotide probe with a cell sample thought to comprise a dopaminergic neuron proliferative progenitor cell, wherein a cell which binds to said polynucleotide probe is identified as a dopaminergic neuron proliferative progenitor cell, wherein the polynucleotide probe identifies the human Lrp4 gene and comprises a sequence selected from the following nucleotide sequences (a) to (c):
  (a) a nucleotide sequence complementary to a nucleotide sequence of SEQ ID NO: 2, wherein the polynucleotide probe has at least 95% homology to the sequence of SEQ ID NO: 2;
  (b) a nucleotide sequence complementary to a nucleotide sequence encoding an amino acid sequence of SEQ ID NO: 4, wherein the polynucleotide probe has at least 95% homology to the sequence encoding the amino acid sequence of SEQ ID NO: 4; and (c) a nucleotide sequence that hybridizes under stringent conditions with a polynucleotide consisting of a nucleotide sequence of SEQ ID NO: 2; wherein the stringent conditions comprise a wash step comprising a wash 2×SSC, 0.1% SDS at 65° C. wherein the polynucleotide probe had at least 95% homology to the sequence of SEQ ID NO: 2.

2. A method of postmitotic selecting a dopaminergic neuron progenitor cell comprising the steps of;

(a) selecting a dopaminergic neuron proliferative progenitor cell using the method of claim 1;

(b) culturing the proliferative progenitor cell selected in (a); and, (c) screening the progenitor cell cultured in (b) using a postmitotic dopaminergic neuron marker.

3. The method of claim 1, wherein the nucleotide sequence of (a) is completely complimentary to the nucleotide sequence of SEQ ID NO: 2.

4. The method of claim 1, wherein the nucleotide sequence of (b) is completely complementary to the nucleotide sequence encoding the amino acid sequence of SEQ ID NO: 4.

* * * * *